United States Patent [19]
Honda et al.

[11] Patent Number: 6,051,722
[45] Date of Patent: Apr. 18, 2000

[54] COMPOUNDS, POLYMERS, RESIN COMPOSITIONS AND NONLINEAR OPTICAL DEVICES

[75] Inventors: Yutaka Honda, Tsuchiura; Iwao Fukuchi, Tsukuba, both of Japan; Kwan-Yue Alex Jen, Morganville, N.J.

[73] Assignee: Hitachi Chemical Company, Ltd., Tokyo, Japan

[21] Appl. No.: 09/110,368

[22] Filed: Jul. 6, 1998

[51] Int. Cl.$^7$ .................................................. C07D 311/76
[52] U.S. Cl. ............................ 549/407; 549/50; 549/236; 544/300; 546/115; 546/268.1; 525/420; 525/422; 525/426; 528/310; 528/322
[58] Field of Search ..................................... 525/420, 422, 525/426; 528/310, 322; 549/50, 236, 407; 544/300; 546/115, 268.1

[56] References Cited

U.S. PATENT DOCUMENTS

| | | | |
|---|---|---|---|
| 4,145,215 | 3/1979 | Van Allan et al. | 96/1 PE |
| 5,514,799 | 5/1996 | Varanasi et al. | 544/300 |

FOREIGN PATENT DOCUMENTS

| | | |
|---|---|---|
| 0 791849 | 8/1997 | European Pat. Off. . |
| 54-021722 | 2/1979 | Japan . |

OTHER PUBLICATIONS

S. Ermer et al., "DCM–polyimide system for triple-stack poled polymer electro–optic devices", Appl. Phys. Lett., 61(19), Nov. 9, 1992, pp. 2272–2274.

S. Ermer et al., "DCM–polyimide system for triple-stack poled polymer electro–optic devices", Proc. SPIE, 1853, pp. 183–192 (1993).

S. Ermer et al., "Synthesis and nonlinearity of triene chromophores containing the cyclohexene ring structure", Chem. Mater., 1997, 9, pp. 1437–1442.

*Primary Examiner*—Amelia Owens
*Attorney, Agent, or Firm*—Pennie & Edmonds LLP

[57] ABSTRACT

The present invention provides, as heteroaromatic compounds made functional so as to be used for nonlinear optical materials, compounds represented by the following general formula (1), and also provides polymers obtained from these and nonlinear optical parts comprising such polymers. In the formula, $Ar^1$ and $Ar^2$ each represents a divalent aromatic group; $R^1$, $R^2$ and $R^3$ each represents an atom or a group independently selected from a hydrogen atom or an alkyl group and an aromatic group; $X^1$ represents a monovalent organic group; n represents an integer of 2 to 12; and $Z^1$ and $Z^2$ each represents a group independently selected from electron attractive functional groups.

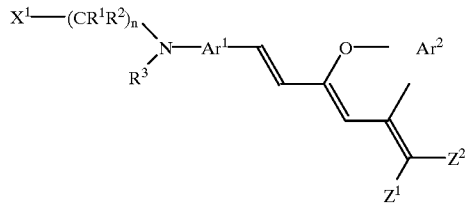

(1)

22 Claims, 9 Drawing Sheets

MACH-ZEHNDER TYPE
WAVEGUIDE SWITCH (ppm)

COMPOUNDS, POLYMERS, RESIN COMPOSITIONS AND NONLINEAR OPTICAL DEVICES

BACKGROUND OF THE INVENTION

1. Technical Field to Which the Invention Belongs

This invention relates to a novel compound and an organic polymer, a resin composition containing them, and nonlinear optical device prepared using the resin composition.

2. Prior Art

Nowadays, materials having nonlinear optical activities (NLO materials) sufficiently highly effective to double or triple the frequency of electromagnetic waves attract great scientific and technical interest as materials usable in optical long-distance communication, signal processing, photoelectric hybrid circuits and optical computers.

Nonlinear optics is concerned with the mutual action of electromagnetic waves in various mediums, which is necessary for generating a new field variable in phase frequency or amplitude, and electro-optic adjustment of electromagnetic waves is represented by, e.g., the following two expressions:

$$\Delta n = -(\tfrac{1}{2}) n^3 r_{33} E$$

$$r_{33} \, \beta\mu$$

In the above, $\Delta n$ is change in refractive index, n is refractive index, $r_{33}$ is electro-optic constant, E is electric-field strength, $\beta$ is secondary nonlinear susceptibility, and $\mu$ is dipole moment. The $r_{33}$ increases with an increase in $\beta\mu$, and therefore $\Delta n$ increases with $\beta\mu$.

As a compound having a secondary nonlinear susceptibility, having a vinylene group between an aromatic ring and a pyran ring, Van Aran et al. discloses 4-(dicyanomethylene-2-methyl-6-(p-dimethylaminostyryl)-4H-pyran (hereinafter "DCM") in Japanese Patent Application Laid-open No. 54-21722 and U.S. Pat. No. 4,145,215.

The DCM, however, has so poor a stability to light or heat that, although it has been possible to prepare an optical device using a secondary nonlinear susceptibility, actually it has been difficult to ensure drive reliability for a time long enough to withstand practical use. For example, Appl. Phys. Lett., 61, pp.2272–2274 (1992) reports a method in which an organic polymer composition having a nonlinearity is produced by a guest-host system where the DCM is added in polyimide, and an electro-optical device constituted of an optical waveguide is fabricated using this composition. In addition thereto, as a chemically modified product of the above compound, having a high thermal stability, PROC. SPIE, 1853, pp.183–192 (1993) also presents a compound having a cyclohexene ring in place of the pyran ring. Chem. Mater., 9(6), pp.1437–1442 (1997) reports some derivatives each having a cyclohexene ring which have a nonlinear ability. In this report, synthesis of novel compounds in which an aromatic ring and a pyran ring are coalesced is reported, but there is no description on the nonlinearity and stability of the compounds.

In the case of the guest-host system utilizing the addition of a nonlinear compound to an organic polymer, there has been a problem that the nonlinear optical characteristics may deteriorate because the nonlinear compound thus added disappears because of thermal diffusion occurring under high-temperature conditions when the composition is cured by heating or when optical devices made from the composition are subjected to annealing or soldering. For example, Appl. Phys. Lett., 61, pp.2272–2274 (1992) reports that 220° C. is the limit in the case of the DCM. Also when the nonlinear compound is kept oriented by a suitable method, there has been a problem that its treatment at a high temperature may make the orientation become loose by heat to cause deterioration of nonlinear optical characteristics. Still also when the composition is prepared by adding the nonlinear compound at a high concentration in a polymer solution, there has been a problem that the compound may deposit because of its crystallization or insolubilization at the time of solvent evaporation or heat curing, to cause a deterioration of film properties and a great propagation loss.

DISCLOSURE OF THE INVENTION

An object of the present invention is to provide an organic polymer and a composition capable of second harmonic generation (SHG), and electro-optic control of electromagnetic waves having a wavelength ranging between 300 nm and 2,000 nm, once oriented by a suitable method, a composition containing the compound, a nonlinear optical element and an optical device which are prepared using them.

To achieve the above object, the present inventors have discovered that a heteroaromatic compound in which a pyran ring having a vinylene group between a first aromatic ring and the pyran ring is coalesced with a second aromatic ring (i.e., which has a condensed ring containing a pyran ring) has a high stability to heat. They have also discovered that a nonlinear organic polymer having a small propagation loss, a great electro-optic effect and a high thermal resistance can be obtained by connecting such a heteroaromatic compound to an organic polymer. They have still also discovered that such a heteroaromatic compound, even at a high concentration, does not cause any deterioration of film properties by insolubilization or the like. It has been made clear that when, e.g., an optical waveguide which transmits light of around 830 nm is produced using the organic polymer of the present invention, a product can be obtained which has a small propagation loss because of its optical transparency sufficient for light transmission and also can withstand a high temperature necessary for the fabrication of devices, e.g., soldering temperature.

As heteroaromatic compounds made functional so as to be used for nonlinear optical materials, the present invention provides the following aromatic compounds A to C and an organic polymer D.

A. A first heteroaromatic compound represented by the following general formula (1).

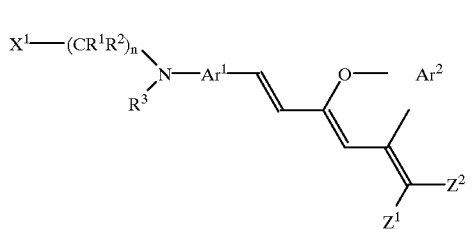

(1)

In the formula (1), $Ar^1$ and $Ar^2$ each represents a divalent aromatic group; $R^1$, $R^2$ and $R^3$ represents an atom or a group independently selected from a hydrogen atom, an alkyl group and an aromatic group; $X^1$ represents a monovalent organic group; n represents an integer of 3 to 12; and $Z^1$ and $Z^2$ each represents a group independently selected from electron attractive functional groups.

B. A second heteroaromatic compound represented by the following general formula (2).

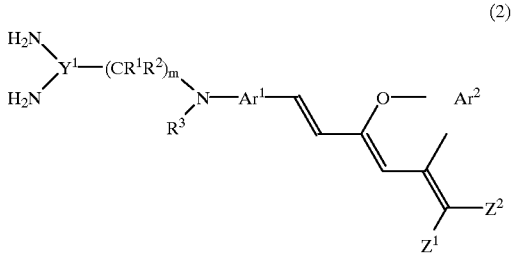

(2)

In the formula (2), $Ar^1$ and $Ar^2$ each represents a divalent aromatic group; $R^1$, $R^2$ and $R^3$ each represents an atom or a group independently selected from a hydrogen atom, an alkyl group and an aromatic group; $Y^1$ represents a trivalent organic group; n represents an integer of 2 to 12; and $Z^1$ and $Z^2$ each represents a group independently selected from electron attractive functional groups.

C. A third heteroaromatic compound represented by the following general formula (10).

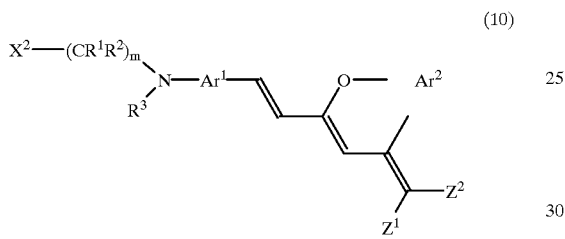

(10)

In the formula (10), $Ar^1$ and $Ar^2$ each represents a divalent aromatic group; $R^1$, $R^2$ and $R^3$ each represents an atom or a group independently selected from a hydrogen atom, an alkyl group and an aromatic group; $X^2$ represents a monovalent organic group having at least one of an aliphatic ring and an aromatic ring; m represents an integer of 2 to 12; and $Z^1$ and $Z^2$ each represents a group independently selected from electron attractive functional groups.

D. A first organic polymer having an atomic group represented by the following general formula (3).

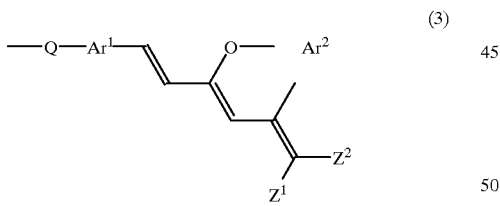

(3)

In the formula (3), $Ar^1$ and $Ar^2$ each represents an aromatic group independently selected; Q represents an electron donative functional group; and $Z^1$ and $Z^2$ each represents a group independently selected from electron attractive functional groups.

In these first to third heteroaromatic compounds and the first organic polymer, $Ar^2$ may preferably have an aromatic ring forming a condensed ring with a pyran ring. More specifically, any two carbon atoms constituting the aromatic ring included in $Ar^2$ may each preferably constitute a pyran ring.

$Ar^1$ and $Ar^2$ are aromatic groups, which may consist of aromatic rings alone or may be substituted aromatic rings to which substituents are bonded, or position isomers of these. $Ar^1$ and $Ar^2$ may each particularly preferably be a benzene ring.

In the first to third heteroaromatic compounds and the first organic polymer, $Z^1$ and $Z^2$ are electron attractive functional groups. The groups $Z^1$ and $Z^2$ may be, e.g., a nitro group, a cyano group, perfluoroalkyl groups such as trifluoromethyl, pentafluoroethyl and heptafluoropropyl, acyl groups, perfluoroacyl groups and a formyl group, and may also be a ketone group, a sulfoxide group, a sulfone group, aryl groups such as a phenyl group, a biphenyl group, a naphthyl group, a pyridinyl group, a pyrimidinyl group, a pyridazinyl group, a thiophenyl group, a pyranyl group and a furanyl group, unsaturated groups such as alkenyl groups and alkynyl groups, and also functional groups comprising such unsaturated groups to which electron attractive groups are connected. The groups $Z^1$ and $Z^2$ may each preferably be a cyano group.

As shown in the following general formulae (13) to (15), $Z^1$ and $Z^2$ may combine with each other to form a ring structure. A general formation process of such a ring structure is disclosed in, for example, U.S. Pat. No. 5,514,799. It is possible to easily form the ring structure using N,N-dialkylbarbituric acid, N,N-dialkylthiobarbituric acid, Rhodamine, hydantoin or exazoline, etc.

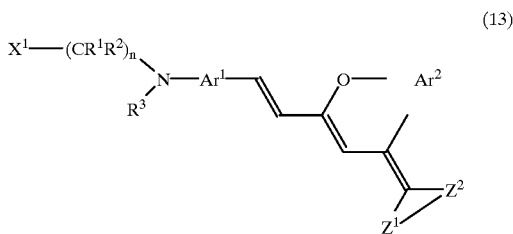

(13)

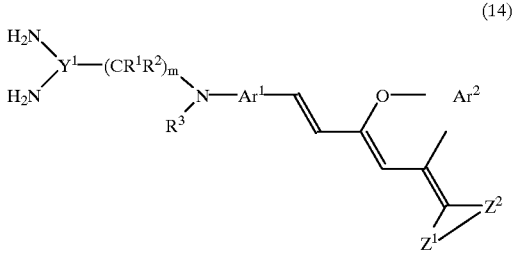

(14)

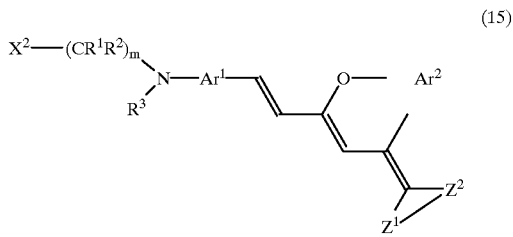

(15)

In the first to third heteroaromatic compounds and the first organic polymer, $X^1$ and $X^2$ may have connective functional groups (or reactive functional groups).

In the second heteroaromatic compound, $Y^1$ may preferably have a structure represented by the following structural formula (8).

(8)

In the formula (8), $Ar^3$ represents a trivalent aromatic group, and $Y^2$ represents a divalent functional group.

In the first organic polymer, Q may preferably have an atomic group represented by the following general formula (4).

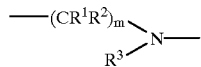
(4)

In the formula (4), $R^1$, $R^2$ and $R^3$ each represents a hydrogen atom or a monovalent organic group; and m represents an integer of 2 to 12.

Of these first to third heteroaromatic compounds, particularly preferred ones may be a compound represented by the following general formulae (7), (9) or (11).

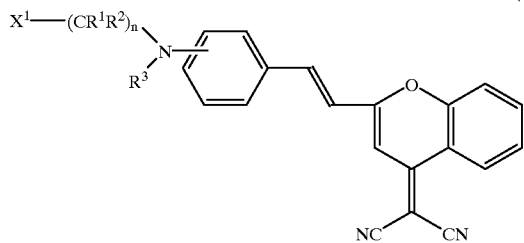
(7)

In formula (7), $R^1$, $R^2$ and $R^3$ each represents an atom or a group independently selected from a hydrogen atom, an alkyl group and an aromatic group; $X^1$ represents a monovalent organic group; n represents an integer of 3 to 12; and $Z^1$ and $Z^2$ each represents a group independently selected from electron attractive functional groups.

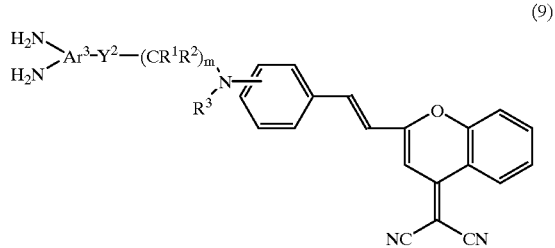
(9)

In the formula (9), $R^1$, $R^2$ and $R^3$ each represents an atom or a group independently selected from a hydrogen atom, an alkyl group and an aromatic group; m represents an integer of 2 to 12; $Ar^3$ represents a trivalent aromatic group; and $Y^2$ represents a divalent functional group.

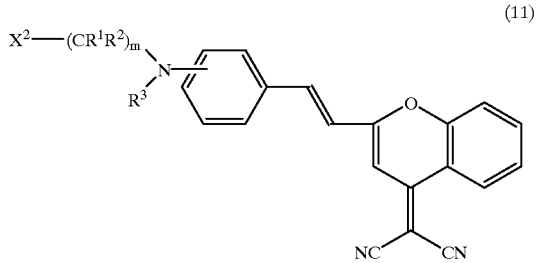
(11)

In the formula (11), $R^1$, $R^2$ and $R^3$ each represents an atom or a group independently selected from a hydrogen atom, an alkyl group and an aromatic group; $X^2$ represents a monovalent organic group; n represents an integer of 3 to 12; and $Z^1$ and $Z^2$ each represents a group independently selected from electron attractive functional groups.

Of the first organic polymers, particularly preferred ones may be those in which the above atomic group is represented by the following general formula (12).

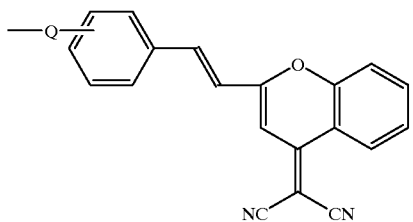
(12)

The first organic polymers of the present invention may include, e.g., polymethacrylates, polyurethane, polyamide, polyimide, polyimide precursors and polyquinoline which have the above atomic group on the side chain in the molecule. It may also include polymers obtained by reacting the heteroaromatic compound of the above formula (2). For example, the heteroaromatic compound of the above formula (2) may be allowed to react with a carboxylic anhydride to obtain a polyimide precursor, and this is also embraced in the first organic polymer of the present invention. A polyimide obtained by heat-curing this polyimide precursor of the present invention is also embraced in the first organic polymer of the present invention. In view of nonlinear optical activities of the resultant polyimide, the carboxylic anhydride used in the synthesis of this polyimide precursor may preferably be a compound represented by the following chemical formula (5).

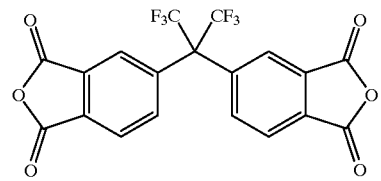
(5)

In the present invention, a copolymer is also provided as a second organic polymer, which is a copolymer produced by mixing at least two polyimide precursors followed by heating and in which at least one of the polyimide precursors is a polyimide precursor obtained by allowing the heteroaromatic compound of the above general formula (2) to react with a carboxylic anhydride. Incidentally, at least one of the remaining polyimide precursors may preferably have a repeating unit represented by the following chemical formula (6).

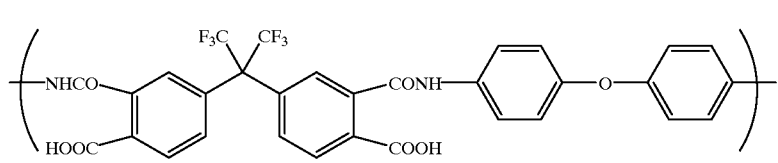

(6)

In the present invention, a polyimide copolymer is still also provided as a third organic polymer, which is obtained by heat-curing the above second organic polymer polyimide precursor.

In the present invention, also provided are a resin composition containing any of the first to third heteroaromatic compounds described above, a fourth organic polymer obtained by curing the resin composition, and an optical device such as a nonlinear device at least a part of which is comprised of any of the first to fourth organic polymers.

The compound (including a polymer) having a nonlinear optical ability and resin composition obtained in the present invention, can be used in optical devices such as optical switches for processing optical signals, e.g., branching, combining or amplifying them when, in photoelectric hybrid circuits, information is exchanged between operation elements and memories using optical wiring. They can also be used in active optical devices employing optical waveguides in signal transmission lines so as to have an active function (for example, branching, combining or amplifying) such as, a switching function, which is used in optical long-distance communication, signal processing, photoelectric hybrid circuits, optical computers and so forth. In the field of optical recording, they can also be applied to wavelength conversion devices that utilize higher-harmonic generation attributable to nonlinear optical effects to convert wavelengths of lasers.

Figure 1:
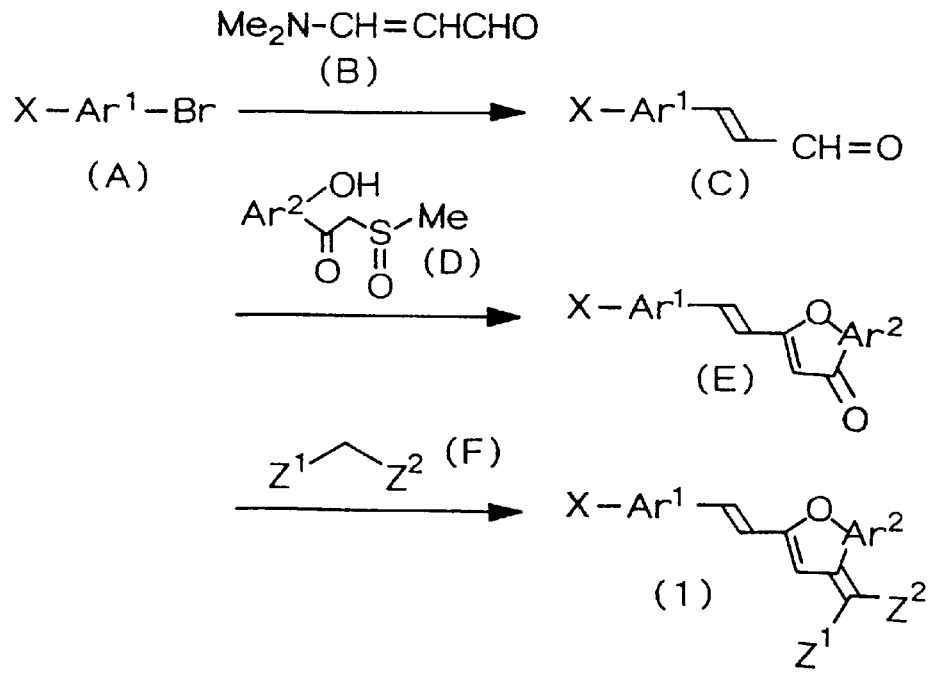
FIGS. 1 to 4 illustrate an example of synthesis route for the heteroaromatic compound of the present invention, respectively.
Figure 2:
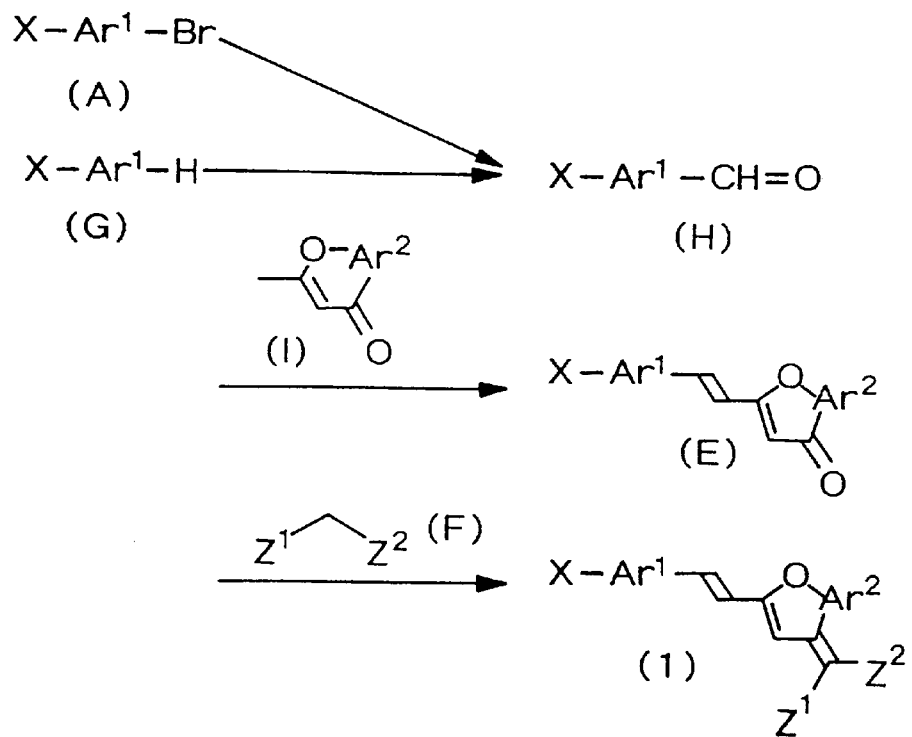

BEST MODES FOR WORKING THE INVENTION (a) Synthesis of the first or third heteroaromatic compound:

Examples of synthesis routes of the first or third heteroaromatic compound are shown in FIGS. 1 and 2. In FIGS. 1 and 2, X is $X^1$—$(CR^1CR^2)_n$—$N(R^3)$— or $X^2$—$(CR^1CR^2)_m$—$N(R^3)$—.

The first heteroaromatic compound represented by the above general formula (1) (hereinafter "compound (1)") and the third heteroaromatic compound represented by the above general formula (10) (hereinafter also "compound (1)") can be synthesized through, e.g., the following steps. First, a halide (A) is treated with a metallizing agent and thereafter condensed with an unsaturated aldehyde agent (B) to derive an aldehyde (C). Next, the compound (C) and a sulfoxide (D) having a phenolic hydroxyl group are condensed to obtain a ketone (E), which is further condensed with a carbon-multiplying agent (F) having an electron attractive functional group, so that a compound (1) can be obtained. The halide (A) or (G) may be converted into an aldehyde (H), which may then be condensed with a heteroaromatic compound (I) to obtain a ketone (E).

The groups $Ar^1$ and $Ar^2$ may be an aromatic ring such as, phenyl-diyl, naphthalene-diyl, biphenyl-diyl, thiophene-diyl, benzo[b]thiophene-diyl, naphtho[2,3-b]thiophene-diyl, thianthrene-diyl, furan-diyl, pyran-diyl, benzo[b]furan-diyl, isobenzofuran-diyl, chromene-diyl, xanthene-diyl, phenoxathin-diyl, 2H-pyrrole-diyl, pyrrole-diyl, imidazole-diyl, pyrazole-diyl, pyridine-diyl, pyrazine-diyl, pyrimidine-diyl, pyridazine-diyl, indolizine-diyl, isoindole-diyl, 3H-indole-diyl, indole-diyl, 1H-indazole-diyl, purine-diyl, 4H-quinolizine-diyl, isoquinoline-diyl, quinoline-diyl, phthalazine-diyl, naphthyridine-diyl, quinoxaline-diyl, quinazoline-diyl, cinnoline-diyl, pteridine-diyl, 4aH-carbazole-diyl, carbazole-diyl, β-carboline-diyl, phenanthridine-diyl, acrydine-diyl, perimidine-diyl, phenanthroline-diyl, phenazine-diyl, phenarsazine-diyl, isothiazole-diyl, phenothiazine-diyl, isoxazole-diyl, furazane-diyl, phenoxazine-diyl, isochroman-diyl, chroman-diyl, pyrrolidine-diyl, pyrroline-diyl, imidazolidine-diyl, imidazoline-diyl, pyrazolidine-diyl, pyrazoline-diyl, piperidine-diyl, piperazine-diyl, indoline-diyl, isoindoline-diyl, quinuclidine-diyl and morpholine-diyl; a derivative of that; or a position isomer of that.

The groups $R^1$, $R^2$ and $R^3$ are each a hydrogen atom, or also may be a saturated hydrocarbon group such as methyl, ethyl, propyl, butyl and pentyl, a saturated cyclic hydrocarbon group such as cyclopentyl and cyclohexyl, an unsaturated hydrocarbon group such as vinyl, allyl, cyclopentenyl, cyclohexenyl, and benzyl, perfluoroalkyl groups such as trifluoromethyl, pentafluoroethyl and heptafluoropropyl, an aromatic group such as phenyl, naphtyl, p-methoxyphenyl and p-dimethylaminophenyl or an isomeric group of that.

The group $X^1$ may be an electron donative group such as alkylamino groups, dialkylamino groups, arylamino groups, dialylamino groups, alkylarylamino groups, aminoalkenyl groups, aminoalkynyl groups, alkyl sulfide groups, arylsulfide groups, alkyloxy groups, aryloxy groups. The alkyl group and the aryl group may have substituents and may further have connective functional groups (inclusive of reactive functional groups).

$X^2$ is a monovalent organic group having at least one of an aliphatic ring and an aromatic ring. Organic polymers having a cyclic structure can have a higher glass transition temperature than those having only a chain structure, to have a higher thermal resistance, and hence the compound (1) having such $X^2$ is preferred. When putting into optical uses, those having less hydrogen atoms may cause smaller light transmission loss, and hence the compound may preferably have an aromatic ring having a smaller number of hydrogen atoms per carbon atom than the aliphatic ring.

The above aliphatic ring or aromatic ring may be a cycloalkane ring such as cyclopropane, cyclobutane, cyclopentane, cyclohexane, cycloheptane and cyclooctane, a cycloalkene ring such as cyclopropene, cyclobutene, cyclopentene, cyclohexene, cycloheptene and cyclooctene, or an aromatic ring such as benzene, biphenyl, naphthalene, pyridine, pyrimidine, pyridazine, thiophene, pyran and furan. These aliphatic rings and aromatic rings may have substituents and may further have a connective functional group (inclusive of a reactive functional group).

The connective functional group may be a hydroxyl group, a phenol group, a sulfide group, an amino group, a carboxyl group, an acetylene group, an aldehyde group, an acetal group, functional groups having an unsaturated double bond such as an acrylate group, a methacrylate group and a styrene group, an epoxy group, and an azido group.

The reactive functional group may be a halogen group such as a fluoro group, a chloro group, a bromo group and an iodo group, a sulfinyloxy group such as a methanesulfinyloxy group, a trifluoromethanesulfinyloxy group, an ethanesulfinyloxy group, a benzenesulfinyloxy group and a p-toluenesulfinyloxy group, and sulfonyloxy groups such as a methanesulfonyloxy group, a trifluoromethanesulfonyloxy group, an ethanesulfonyloxy group, a benzenesulfonyloxy group and a p-toluenesulfonyloxy group.

As specific examples of the compound (1), it may include the following compounds 1a to 1h.

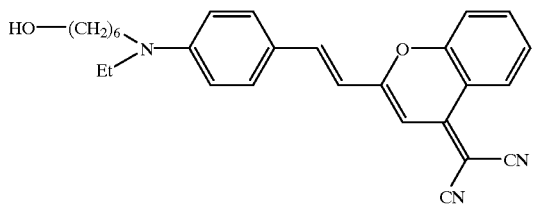

(1a)

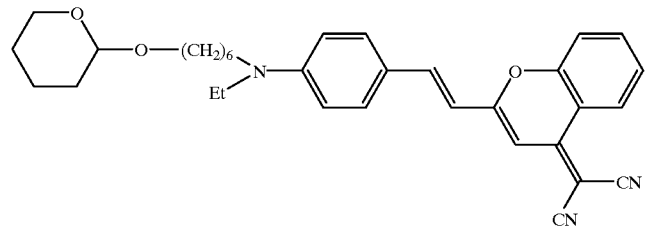

(1b)

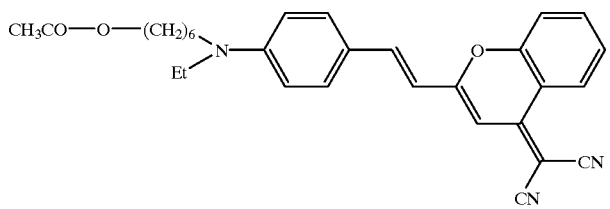

(1c)

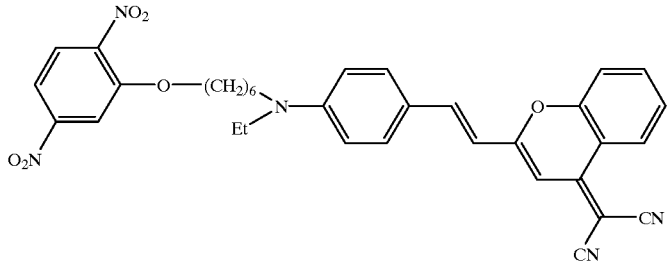

(1d)

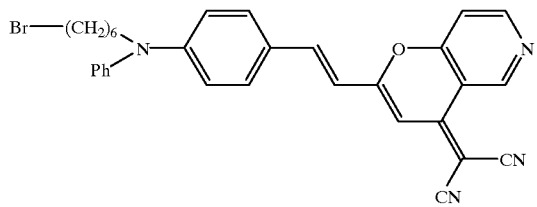

(1e)

-continued

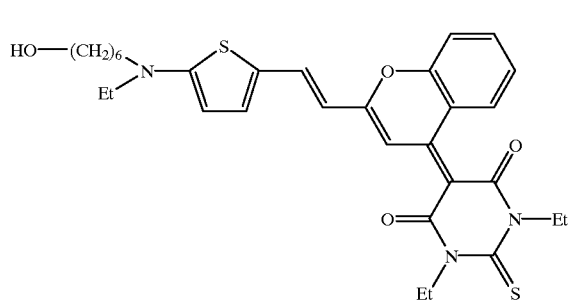

(1f)

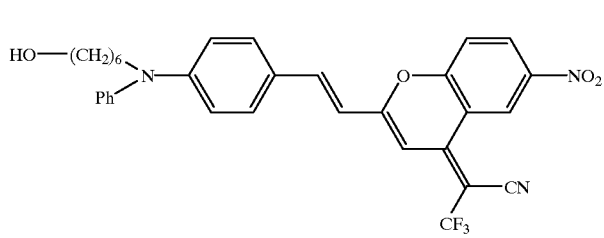

(1g)

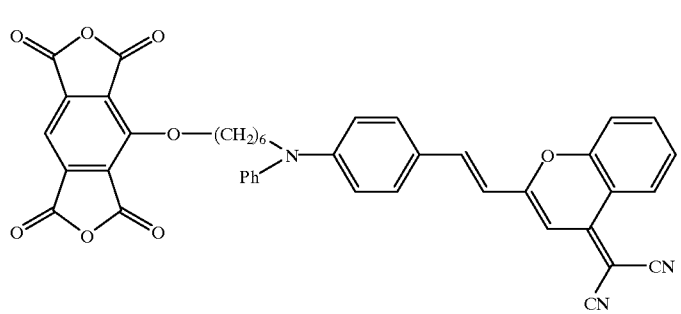

(1h)

In a case where the compound (1) in which $X^1$ or $X^2$ has a hydroxyl group is synthesized through the synthesis route shown in FIG. 1, the hydroxyl group may preferably be protected with a protective group in advance.

The protective group includes heterocyclic protective groups containing an oxygen atom, such as a tetrahydrofuran-2-yl group and a tetrahydropyran-2-yl group, acyl groups such as an acetyl group and a benzoyl group, a triphenylmethyl group, protective groups which can be de-protected under acidic conditions as exemplified by silyl groups such as a trimethylsilyl group, a triphenylsilyl group and a diphenylmethylsilyl group, protective groups which can be de-protected under base hydrolytic conditions, such as an acetyl group and a benzoyl group, and protective groups which can be de-protected with a Lewis acid, such as a methyl group and a triphenylmethyl group.

In a case where the above protective groups can be de-protected under acidic conditions, the compound (1) may be de-protected with an acid, whereby it can be converted into the compound (1) having a hydroxyl group. The acid used here may include mineral acids such as hydrochloric acid, nitric acid, phosphoric acid and boric acid, sulfonic acids such as methanesulfonic acid, p-toluenesulfonic acid and trifluoromethanesulfonic acid, and carboxylic acids such as formic acid, acetic acid and trifluoroacetic acid. As a solvent used in this instance, it may include water, alcohols such as methanol and ethanol, ethers such as diethyl ether, tetrahydrofuran and dioxane, aromatic solvents such as benzene, toluene and xylene, halogen type solvents such as dichloromethane and chloroform, and mixtures of any of these. When the acid is liquid, the acid itself may be used. There are no particular limitations on the reaction temperature. The reaction is accelerated under application of heat. As other reaction conditions, oxygen and light may preferably be shut out.

In a case where the above protective groups can be de-protected under base hydrolytic conditions, the compound (1) may be de-protected with a base, whereby it can be converted into the compound (1) having a hydroxyl group. The base used here may include hydroxides such as potassium hydroxide, sodium hydroxide and barium hydroxide, metal alkoxides such as sodium methoxide and potassium tertiary butoxide, ammonia water, and metal amides such as sodium amide. As a solvent used in this instance, it may include water, alcohols such as methanol and ethanol, ethers such as diethyl ether, tetrahydrofuran and dioxane, aromatic solvents such as benzene, toluene and xylene, and mixtures of any of these. There are no particular limitations on the reaction temperature. The reaction is accelerated under application of heat. As other reaction conditions, oxygen and light may preferably be shut out.

In a case where the above protective groups can be de-protected with a Lewis acid, the compound (1) may be de-protected with a Lewis acid, whereby it can be converted into the compound (1) having a hydroxyl group. The Lewis acid used here may include aluminum chloride, ferrous chloride, ferric chloride, ferrous sulfate and ferric sulfate. As a solvent used in this instance, it may include halogen type solvents such as dichloromethane and chloroform. As reaction conditions, anhydrous conditions are necessary, and oxygen and light may preferably be shut out. There are no particular limitations on the reaction temperature. Side reaction is prohibited at a low temperature.

(b) Synthesis of the second heteroaromatic compound:

A process for synthesizing the second heteroaromatic compound represented by the general formula (2) (hereinafter "compound (2)") will be described below taking as an example a compound wherein $Y^1$ is a group represented by the above structural formula (8) when $y^2$ is —O— (hereinafter "compound (2')").

Figure 3:
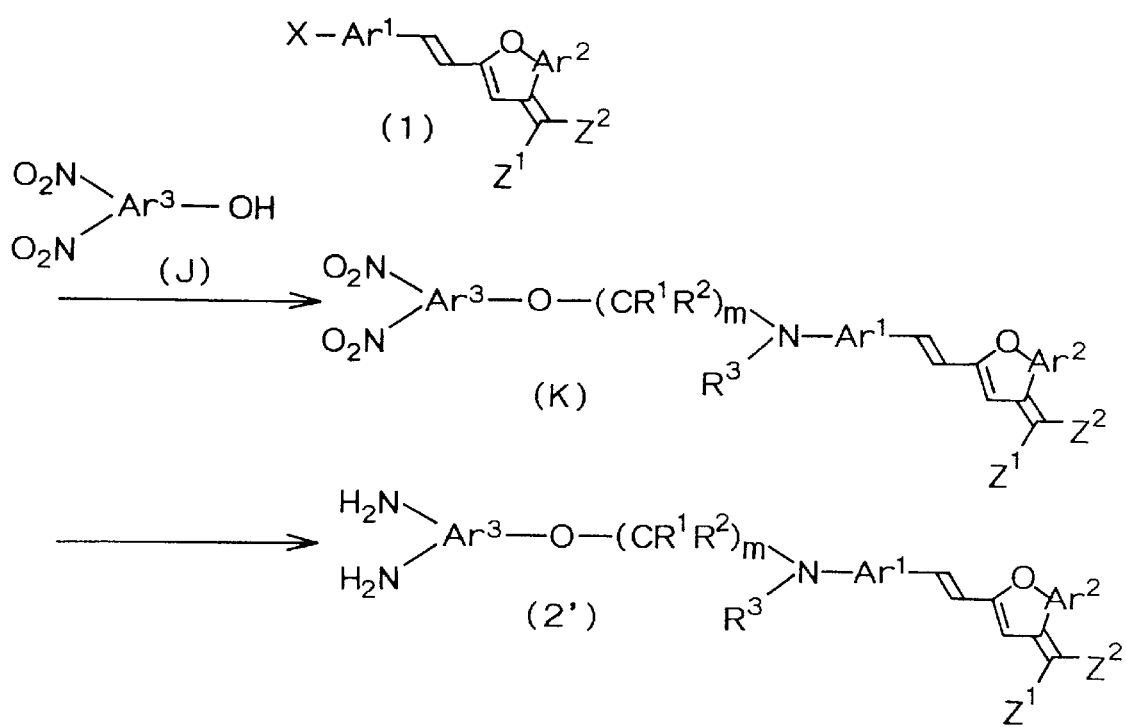

When the functional group $X^1$ or $X^2$ of the compound (1) has an eliminable reactive group, the compound (2) can be obtained through, e.g., the synthesis route shown in FIG. 3. More specifically, the compound (1) and phenol (J) are subjected to condensation reaction to obtain a dinitro compound (K), and this may be reduced to obtain a diamino compound, the compound (2').

In a case where the compound (1) has a halogen group or a sulfonate group as the eliminable reactive group, the phenolic hydroxyl group of a compound (J) may be treated with a metallizing agent to effect metallization reaction, and the resultant compound may be condensed with the compound (1), whereby, e.g., a dinitro compound (K) can be obtained.

There are no particular limitations on the temperature for the metallization reaction. A temperature of 0° C. or below is preferred because the agent can be restrained from decomposition. There are no particular limitations on the temperature for the condensation reaction. Heating conditions are preferred because the reaction can be accelerated. Also, this condensation reaction may preferably be carried out in an environment from which oxygen, light and water have been shut out.

The metallizing agent used here in the condensation reaction may include hydride metallizing agents such as potassium hydride, lithium hydride, sodium hydride and calcium hydride, and metallizing hydrocarbons such as n-butyl lithium, sec-butyl lithium, phenyl lithium, methyl lithium, ethyl magnesium bromide.

Solvents usable in this condensation reaction may include ethers such as diethyl ether, tetrahydrofuran and dioxane, aromatic solvents such as benzene, toluene and xylene, halogen type solvents such as o-dichlorobenzene, and mixtures of any of these.

In a case where the compound (1) has a hydroxyl group as the eliminable reactive group, it may be condensed with a compound (J) in the presence of a condensation agent, whereby, e.g., a dinitro compound (K) can be obtained.

This condensation reaction may preferably be carried out in an environment from which oxygen and light have been shut out. There are no particular limitations on the reaction temperature. Heating conditions are preferred because the reaction can be accelerated.

As a condensing reagent used in this condensation reaction, a triarylphosphine such as triphenylphosphine and a dialkyl azodicarboxylate such as diethyl azodicarboxylate are used in combination. As a solvent used in this condensation reaction, it may include ethers such as diethyl ether, tetrahydrofuran and dioxane, aromatic solvents such as benzene, toluene and xylene, halogen type solvents such as dichloromethane and chloroform, and mixtures of any of these.

The nitro groups of the dinitro compound (K) are reduced, whereupon the diamine compound (2') can be obtained. A reducing agent used here in the reduction reaction may include hydrogen sulfide, hydrogen sulfide-triphenylphosphine, hydrazine hydrate, sodium hydrogen sulfide, ammonium sulfide, polysulfide, stannous chloride and stannous chloride hydrate. Stannous chloride and stannous chloride hydrate are preferred.

As a solvent used in this reduction reaction, it may include water, hydrochloric acid, alcohols such as methanol and ethanol, ethers such as diethyl ether, tetrahydrofuran and dioxane, esters such as methyl acetate and ethyl acetate, aromatic solvents such as benzene, toluene and xylene, halogen type solvents such as dichloromethane and chloroform, and mixtures of any of these. In a case where the stannous chloride or stannous chloride hydrate is used as the reducing agent, it is preferable to use hydrochloric acid as the solvent.

In a case where hydrochloric acid is used as the solvent, the reaction mixture obtained after the reaction may preferably be neutralized with a base such as sodium carbonate, potassium carbonate, sodium hydroxide or potassium hydroxide so that the amino group formed is liberated to make the subsequent extraction easy. There are no particular limitations on the reaction temperature. The reaction is accelerated under application of heat in some cases. As other reaction conditions, oxygen and light may preferably be shut out.

Figure 4:
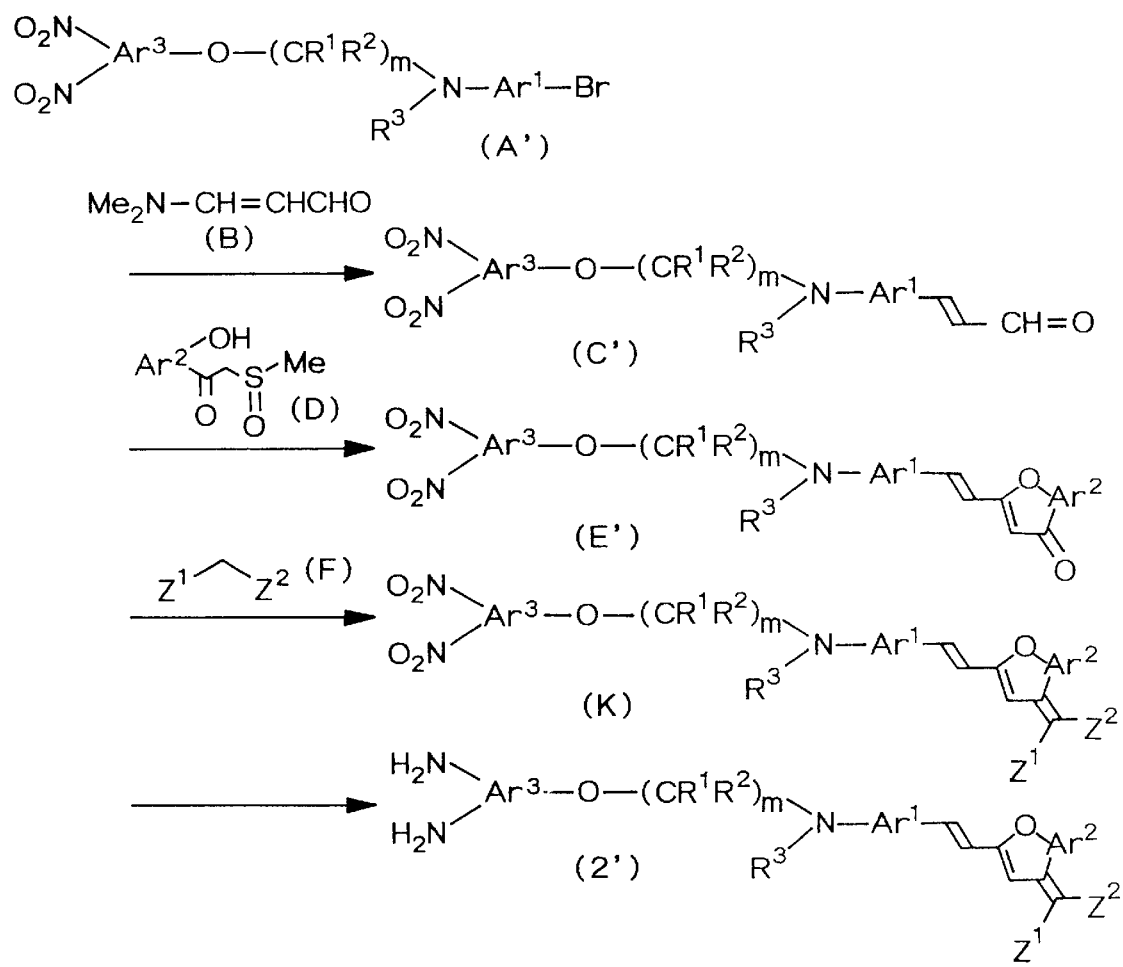

As shown in FIG. 4, it is also possible to obtain a dinitroaldehyde (C') from a dinitrohalide (A') and to derive therefrom the compound (2') being a diamino compound, in the same manner as the steps shown in FIG. 1. In the example shown in FIG. 4. bromine is used as the eliminable reactive group. Halogen groups such as a fluorine group, a chlorine group, a bromine group and an iodine group, sulfonate groups such as a methanesulfonyloxy group and a p-toluene sulfonyloxy group and a p-toluenesulfonyloxy group, an amino group, and a nitroso group may also be used.

The aromatic ring constituting the group $Ar^3$ of the compound (2) may be benzene, naphthalene, biphenyl, thiophene, benzo[b]thiophene, naphtho[2,3-b]thiophene, thianthrene, furan, pyran, benzo[b]furan, isobenzofuran, chromene, xanthene, phenoxathin, 2H-pyrrole, pyrrole, imidazole, pyrazole, pyridine, pyrazine, pyrimidine, pyridazine, indolizine, isoindole, 3H-indole, indole, 1H-indazole, purine, 4H-quinolizine, isoquinoline, quinoline, phthalazine, naphthyridine, quinoxaline, quinazoline, cinnoline, pteridine, 4aH-carbazole, carbazole, β-carboline, phenanthridine, acrydine, perimidine, phenanthroline, phenazine, phenarsazine, isothiazole, phenothiazine, isoxazole, furazane, phenoxazine, isochroman, chroman, pyrrolidine, pyrroline, imidazolidine, imidazoline, pyrazolidine, pyrazoline, piperidine, piperazine, indoline, isoindoline, quinuclidine and morpholine.

$Ar^3$ may consist of any of these aromatic rings alone, or may be a substituted aromatic ring to which a substituent is bonded, or a position isomer thereof.

As specific examples of the compound (2), it may include the following compounds 2a to 2e.

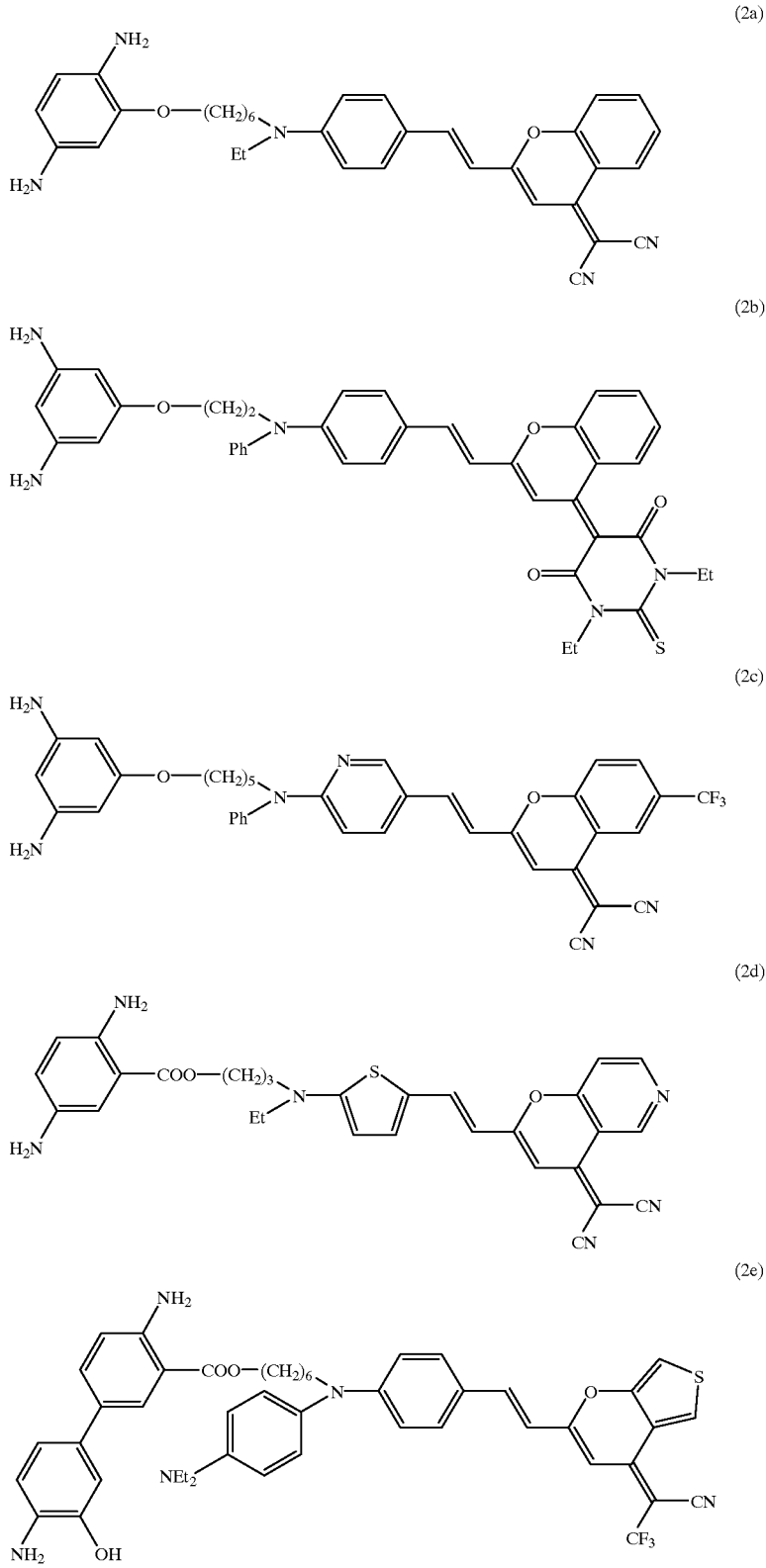

(c) Synthesis of the organic polymers:

There are no particular limitations on the first organic polymer of the present invention, i.e., the organic polymer having the atomic group represented by the above general formula (3). It may be polyacrylate, polymethacrylate, polyacrylamide, polycarbonate, polysiloxane, polyamide, polyimide, polyester, polystyrene, polyether ketone, polyether ether ketones, polyphenyl ether ketone, polybenzocyclobutene or polyquinoline. As polyimide resins contained in the first organic polymer, they may be polyimide, polyamide-imide, polybenzimidazole, polyether imide, polyester imide, or polyisoimide. When putting into optical uses, those in which hydrogen atoms (preferably all the hydrogen atoms) have been substituted with fluorine or heavy hydrogen are preferred because of their small light transmission loss.

The above organic polymer is produced, e.g., in the following way: A compound having a connective functional group or reactive functional group and also having the atomic group represented by the above general formula (3) is mixed with a monomer, a monomer composition, a polymer precursor composition, a polymer precursor or a polymer composition having connective functional groups (including reactive functional groups) to allow them to react to effect chemical bonding. Here, means for the chemical bonding may be covalent bonding, ionic bonding, coordinate bonding or hydrogen bonding.

As the connective function groups, they may be an epoxy group, a carboxylic acid group, a carboxylic anhydride group, a carboxylic halide group, a sulfonic acid group, a sulfonyl halide group a sulfinic acid group, a sulfinyl halide group, a phenolic hydroxyl group, an alkenyl group, a double-bond group, an acryloyl group, a methacryloyl group, an azide group, a chloromethyl group, an acetylene group, a cinnamic acid derivative group, a thiol group, a formyl group, an acetal group, an isocyanate group, a thioisocyanate group, a maleimide group, a cyano group, a halogen group, a hydroxyl group, an amine group, an alkylamine group, an arylamine group, an ester group, a cinnamilidene group, a diazo group, a dithiocarbamate group, a quinone group or a quinone dioxime group.

As examples of processes for producing the first organic polymer, first, the compound (2) diamine is treated into an amide, with a methacryloyl halide in an organic solvent in the presence of a base to synthesize a bismethacrylamide monomer. This monomer may be polymerized, thus a poly (bismethacrylamide) having the atomic group represented by the above general formula (3) can be synthesized.

As another example, an epoxy compound may be polymerized using the compound (2) as an initiator, thus a pendant type epoxy resin having the atomic group represented by the above general formula (3) can be synthesized.

As still another example, an organic polymer can be synthesized using the compound (1). For example, the compound (1) having a hydroxyl group may be esterified using a methacryloyl halide in an organic solvent in the presence of a base, thus a methacrylate monomer can be synthesized. This monomer may be polymerized, thus a polymethacrylate having the atomic group represented by the above general formula (3) can be synthesized.

As still another example, a polymer having a phenolic hydroxyl group and the compound (1) having a hydroxyl group may be treated so as to be formed into an ether by the use of triphenylphosphine and dialkylazodicarboxylate, whereby a pendant type polymer having the atomic group represented by the above general formula (3) can be synthesized. As to the polymer having a phenolic hydroxyl group, some production processes are known. For example, a polyimide having a phenolic hydroxyl group can be produced from 4,4'-diamino-2,2'-dihydroxybiphenyl or 4,4'-diamino-3,3'-dihydroxy-4,4'-biphenyl and carboxylic dianhydride. Also, base hydrolysis of poly(4-acetyloxystyrene) enables production of poly(4-hydroxystyrene).

As examples of the atomic group represented by the general formula (3), it may be an atomic group in 3a to 3e.

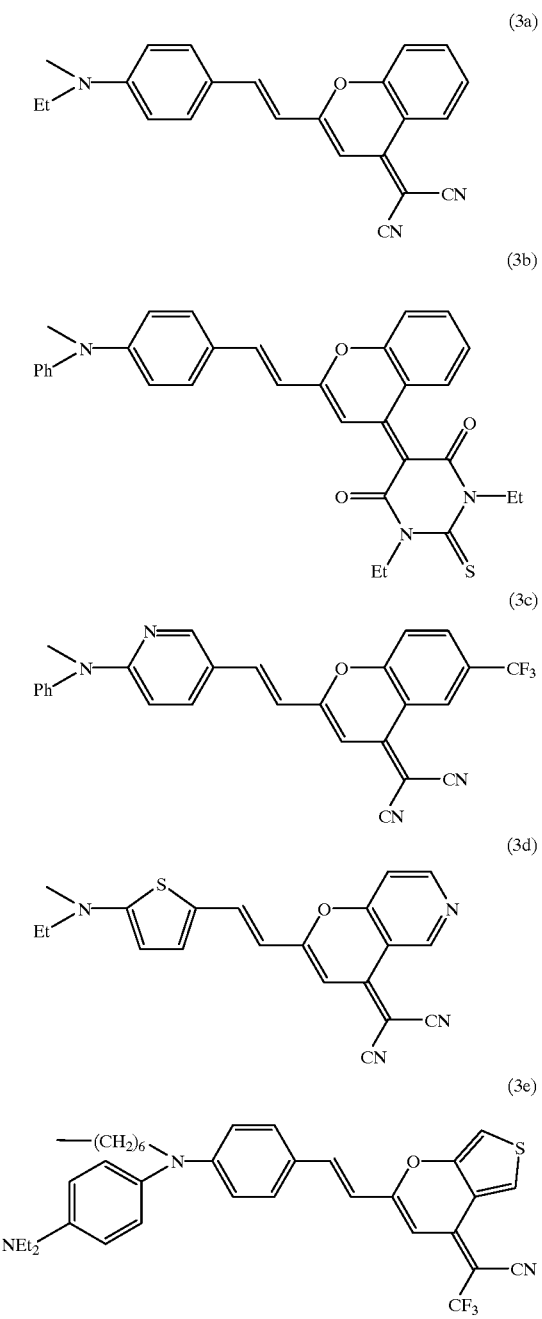

Since the compound (2) is a diamine, it may be allowed to react with a carboxylic anhydride to obtain a polyimide or a precursor thereof.

Here, the polyimide precursor includes polyamic acids, polyamic acid halides, polyamic acid esterified products, and polyimide resins such as polyisoimides. The polyimide includes all products having different degrees of imidization, ranging from polyimide precursors to those completely imidized. In addition to such polyimides, it also includes polyamide-imides, polybenzimidazole, polyether imides, polyester imides, and polyisoimides, polysiloxyimides.

As examples of processes for producing the polyimide and polyimide precursor of the present invention, synthesis routes where the compound (1) in which $X^1$ or $X^2$ has a connective functional group is used will be described with reference to FIGS. 5 and 6.

Figure 5:
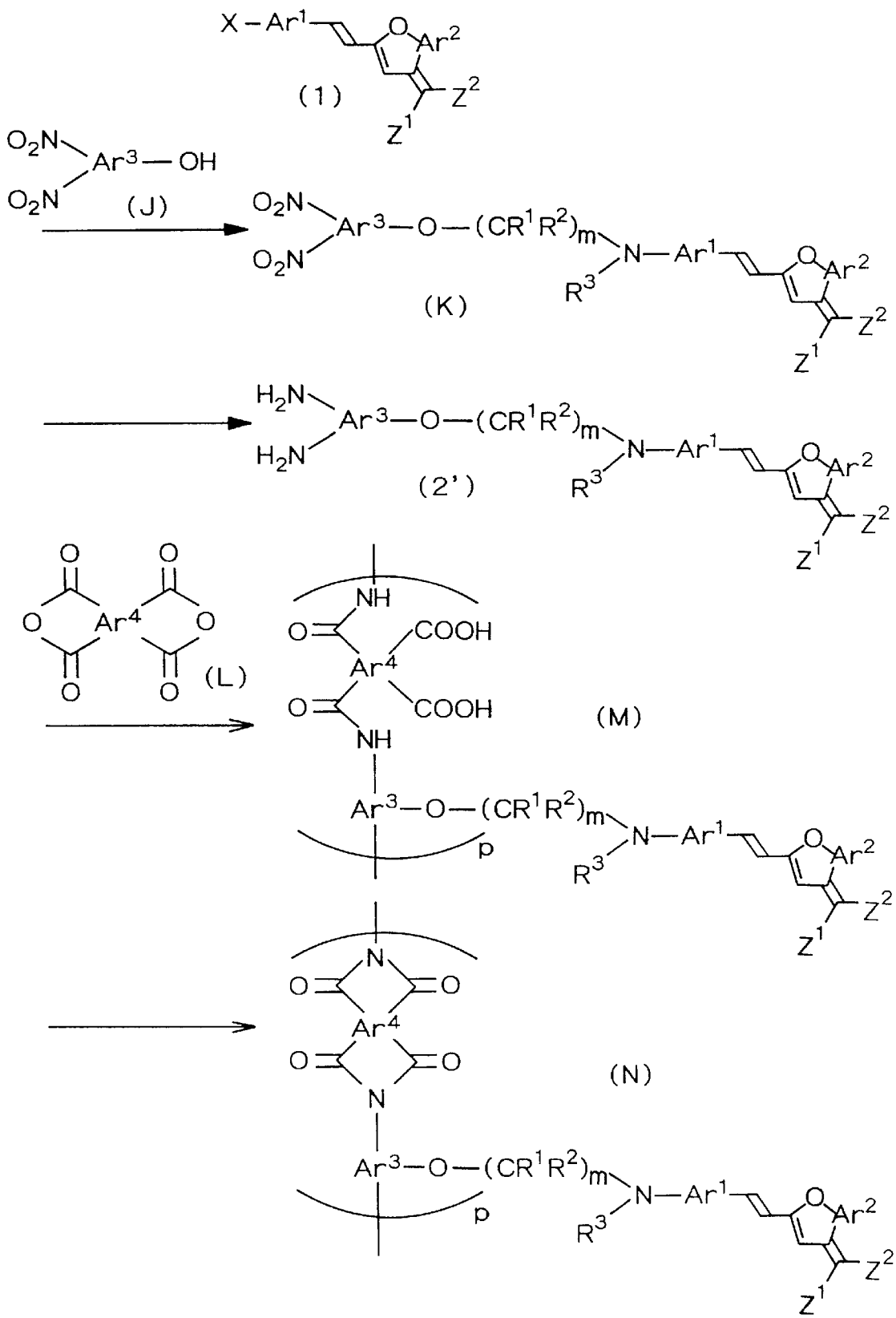
FIGS. 5 and 6 illustrate an example of synthesis route for the polyimide and polyimide precursor of the present invention, respectively.

In the first example of the production process shown in FIG. 5, first, as described above, the compound (1) is condensed with a dinitrophenol (J) to obtain a dinitro compound (K), which is then reduced to convert it into a diamine monomer compound (2') corresponding to the compound of the general formula (2), which is then allowed to react with an acid anhydride (L) to obtain a polyimide precursor polyamide acid (M). This may be heat-cured, thus a polyimide (N) of the present invention can be obtained. In FIG. 5, p is an unspecified integer.

Figure 6:
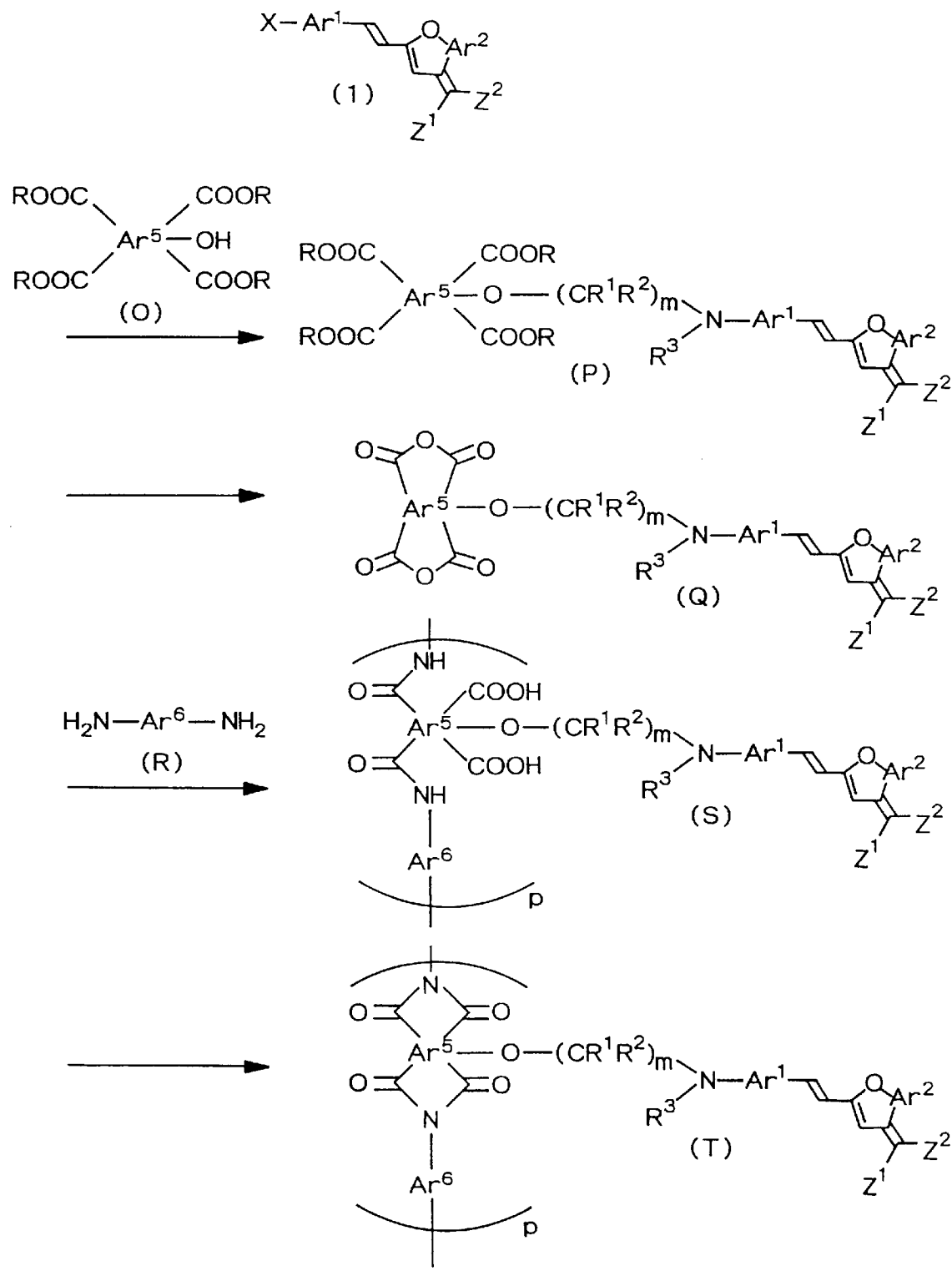

In the second example of the production process shown in FIG. 6, first, the compound (1) is condensed with a hydroxytetracarboxylate (O) to obtain an ester (P). This is hydrolyzed and thereafter formed into an anhydride to convert it into a compound (Q), which is further allowed to react with a diamine (R) to obtain a polyimide precursor polyamide acid (S). This polyamide acid (S) may be heat-cured, thus a polyimide (T) of the present invention can be obtained. In FIG. 6, p is an unspecified integer.

When polyimide or a precursor thereof is produced, the carboxylic anhydride used may include dicarboxylic anhydrides, tricarboxylic anhydrides, tricarboxylic anhydride monohalides, tricarboxylic anhydride monoesters, and tetracarboxylic dianhydrides as will be shown below. Tetracarboxylic dianhydrides are preferred, but not limited to these ones.

Of the tetracarboxylic dianhydrides, preferable compounds may include the following:
2,2-bis(3,4-dicarboxyphenyl)hexafluoropropane dianhydride,
1,2,4,5-benzenetetracarboxylic dianhydride,
3-trifluoromethyl-1,2,4,5-benzenetetracarboxylic dianhydride,
3,6-bis(trifluoromethylmethyl)-1,2,4,5-benzenetetracarboxylic dianhydride,
3,6-difluoro-1,2,4,5-benzenetetracarboxylic dianhydride,
2,3,6,7-naphthalenetetracarboxylic dianhydride,
1,4,5,8-tetrafluoro-2,3,6,7-naphthalenetetracarboxylic dianhydride,
2,3,6,7-tetrafluoro-1,4,5,8-naphthalenetetracarboxylic dianhydride,
1,2,4,5-cyclohexanetetracarboxylic dianhydride,
1,2,3,4-cyclobutanetetracarboxylic dianhydride,
bis(3,4-dicarboxyphenyl) dianhydride,
bis(3,4-dicarboxyphenyl) ether dianhydride,
bis(3,4-dicarboxyphenyl) sulfone dianhydride,
bis(3,4-dicarboxyphenyl) ketone dianhydride,
bis(3,4-dicarboxyphenyl)methane dianhydride,
bis[(3,4-dicarboxyphenyl)dimethylsilyl] ether dianhydride,
2,2-bis(3,4-dicarboxyphenyl)propane dianhydride,
2,2-bis(3,4-dicarboxyphenyl)-1,1,3,3-tetrafluoropropane dianhydride,
1,4-bis(3,4-dicarboxyphenyl)benzene dianhydride,
2,2-bis[4-(3,4-dicarboxyphenyloxy)phenyl]dodecane dianhydride,
2,2-bis[4-(3,4-dicarboxyphenyloxy)phenyl]tridecane dianhydride,
1,4-bis(3,4-dicarboxyphenyloxy)benzene dianhydride,
2,3,5,6-tetrafluoro-1,4-bis(3,4-dicarboxy-2,5,6-trifluorophenyloxy)benzene dianhydride,
bis(3,4-dicarboxy)cyclohexyl dianhydride,
bis(1,2-dicarboxyethyl) dianhydride, and
alkanediol bis(trimellitic anhydride) but not limited to these examples. These acid dianhydrides may be used in the form of a mixture of two or more kinds. In the alkanediol bis(trimellitic anhydride), the alkanes may preferably be those having 2 to 12 carbon atoms.

As examples of the tricarboxylic anhydrides, they may include trimellitic anhydrides and 4-hydroxycarbonylcyclohexanedicarboxylic anhydride. As examples of the tricarboxylic anhydride monohalides, they may include trimellitic anhydride chloride, trimellitic anhydride bromide and 4-chlorocarbonylcyclohexanedicarboxylic anhydride.

As examples of the tricarboxylic anhydride esterified products, they may include methyl trimellitate anhydride, ethyl trimellitate anhydride, propyl trimellitate anhydride, 4-methoxycarbonylcyclohexanedicarboxylic anhydride, and 4-ethoxycarbonylcyclohexanedicarboxylic anhydride.

When putting into optical uses, those in which hydrogen atoms (preferably all the hydrogen atoms) have been substituted with fluorine or heavy hydrogen are preferred because of their small light transmission loss. For example, an acid anhydride represented by the following chemical formula (5) has a high degree of fluorine substitution, and is preferred in view of optical characteristics or the like.

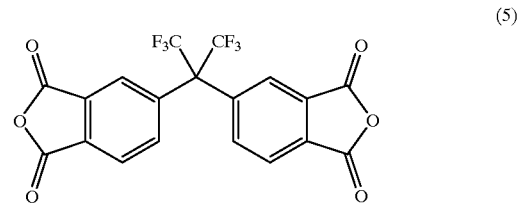

(5)

In the production of the polyimide precursor described above, part or the whole of polyimide precursor may be formed into polyimide. For example, the temperature of the reaction to produce the polyimide precursor may be set within the range of from 50° C. to the boiling point of the solvent and preferably the water generated may be removed from the system, whereby polyimide precursors having different degrees of imidization can be obtained. Here, an agent capable of forming a eutectic mixture with water, such as benzene, ethanol, toluene or xylene, may be added to control the rate of reaction.

As solvents for the reaction to produce this polyimide and/or polyimide precursor, it is possible to use amide type solvents such as N,N-diemthylformamide, N,N-diemthylacetamide and N-methyl-2-pyrrolidinone, ether type solvents such as diethyl ether, tetrahydrofuran, dioxane and diglyme, aromatic solvents such as benzene, toluene and xylene, and mixtures of any of these. In particular, amide type solvents or e ther type solvents are preferred.

The reaction to produce the polyimide precursor may preferably be carried out at a temperature of from 0 to 50° C. In order to make the polyimide or polyimide precursor thereof have a large molecular weight, a low temperature of from 0 to 50° C. is selected. In order to make it easy to cause the cleavage and recombination reaction of amide bonds, a temperature of 30° C. or above is selected. Accordingly, the reaction may be once carried out at a low temperature to make the molecular weight higher, and thereafter at a temperature of 30° C. or above to make the molecular weight lower thereby control viscosity.

The imidization reaction may preferably be carried out at a temperature of 50° C. or above when carried out with heating. In order to complete the imidization, the temperature must be made higher than the glass transition point in some cases. It may also be carried out using a dehydrating agent including trialkylsilyl halides such as trimethylsilyl chloride and triethylsilyl chloride, and N,N'-dialkyl carbodiimide such as N,N'-dicyclohexyl carbodiimide and N,N'- diisopropyl carbodiimide. In such a case, the reaction may preferably be carried out at a temperature of 50° C. or below.

The present invention further provides a copolymer produced by mixing and heating a first polyimide precursor obtained by allowing the compound (2) to react with the carboxylic anhydride and the other polyimide precursor, and provides a polyimide copolymer obtained by heating the above copolymer to cure. The polyimide copolymer can also be obtained by mixing and heating i) a first polyimide obtained by mixing and heating a first polyimide precursor obtained by allowing the compound (2) to react with the carboxylic anhydride and ii) a second polyimide obtained by heating a second polyimide precursor to cure.

As solvents used in the above mixing and heating treatment, it is possible to use amide type solvents such as N,N-dimethylformamide, N,N-dimethylacetamide and N-methyl-2-pyrrolidinone, ether type solvents such as diethyl ether, tetrahydrofuran, dioxane and diglyme, aromatic solvents such as benzene, toluene and xylene, and mixtures of any of these. In particular, amide type solvents or ether type solvents are preferred.

The cleavage and recombination reaction of amide bonds may readily take place when the above treatment is carried out at a temperature of 30° C. or above. Hence, the mixing and heating treatment makes polyimdes or precursors thereof having different constituent units present as equally as possible and makes the system uniform, and is useful for optimizing electro-optic characteristics and film forming properties.

As the other polyimide precursor, a polyimide precursor obtained by allowing the acid anhydride previously described to react with a diamine may be used. The diamine usable here may preferably include the following:

3,3'-diamino-2,2'-dimethylbiphenyl,
3,3'-diamino-2,2'-bis(trifluoromethyl)biphenyl,
3,3'-diamino-2,2'-difluorobiphenyl,
3,3'-diamino-4,4'-dimethylbiphenyl,
3,3'-diamino-4,4'-bis(trifluoromethyl)biphenyl,
3,3'-diamino-4,4'-difluorobiphenyl,
3,3'-diamino-2,2'-dihydroxybiphenyl,
3,3'-diamino-4,4'-dihydroxybiphenyl,
2,2'-diamino-4,4', 5,5,6,6-octafluorobiphenyl,
4,4'-diamino-2,2'-dimethylbiphenyl,
4,4'-diamino-2,2'-bis(trifluoromethyl)biphenyl,
4,4'-diamino-2,2'-difluorobiphenyl,
4,4'-diamino-3,3'-dimethylbiphenyl,
4,4'-diamino-3,3'-bis(trifluoromethyl)biphenyl,
4,4'-diamino-3,3'-difluorobiphenyl,
4,4'-diamino-2,2'-dihydroxybiphenyl,
4,4'-diamino-3,3'-dihydroxybiphenyl,
4,4'-diamino-2,2',3,3',5,5',6,6'-octafluorobiphenyl,
bis(3-aminophenyl) ether,
bis(3-amino-2-methylphenyl) ether,
bis(3-amino-4-methylphenyl) ether,
bis(3-amino-2-trifluoromethylphenyl) ether,
bis(3-amino-4-trifluoromethylphenyl) ether,
bis(3-aminophenyl) thioether,
bis(3-amino-2-methylphenyl) thioether,
bis(3-amino-4-methylphenyl) thioether,
bis(3-amino-2-trifluoromethylphenyl) thioether,
bis(3-amino-4-trifluoromethylphenyl) thioether,
bis(3-aminophenyl) sulfone,
bis(3-amino-2-methylphenyl) sulfone,
bis(3-amino-4-methylphenyl) sulfone,
bis(3-amino-2-trifluoromethylphenyl) sulfone,
bis(3-amino-4-trifluoromethylphenyl) sulfone,
bis(3-aminophenyl) methane,
bis(3-amino-2-methylphenyl) methane,
bis(3-amino-4-methylphenyl) methane,
bis(3-amino-2-trifluoromethylphenyl) methane,
bis(3-amino-4-trifluoromethylphenyl) methane,
bis(4-aminophenyl) ether,
bis(4-amino-2-methylphenyl) ether,
bis(4-amino-3-methylphenyl) ether,
bis(4-amino-2-trifluoromethylphenyl) ether,
bis(4-amino-3-trifluoromethylphenyl) ether,
bis(4-aminophenyl) thioether,
bis(4-amino-2-methylphenyl) thioether,
bis(4-amino-3-methylphenyl) thioether,
bis(4-amino-2-trifluoromethylphenyl) thioether,
bis(4-amino-3-trifluoromethylphenyl) thioether,
bis(4-aminophenyl) sulfone,
bis(4-amino-2-methylphenyl) sulfone,
bis(4-amino-3-methylphenyl) sulfone,
bis(4-amino-2-trifluoromethylphenyl) sulfone,
bis(4-amino-3-trifluoromethylphenyl) sulfone,
bis(4-aminophenyl) methane,
bis(4-amino-2-methylphenyl) methane,
bis(4-amino-3-methylphenyl) methane,
bis(4-amino-2-trifluoromethylphenyl) methane,
bis(4-amino-3-trifluoromethylphenyl) methane,
2,2-bis(3-aminophenyl) propane,
2,2-bis(3-amino-2-methylphenyl)propane,
2,2-bis(3-amino-4-methylphenyl)propane,
2,2-bis(3-amino-2-trifluoromethylphenyl)propane,
2,2-bis(3-amino-4-trifluoromethylphenyl)propane,
2,2-bis(4-aminophenyl)propane,
2,2-bis(4-amino-2-methylphenyl)propane,
2,2-bis(4-amino-3-methylphenyl)propane,
2,2-bis(4-amino-2-trifluoromethylphenyl)propane,
2,2-bis(4-amino-3-trifluoromethylphenyl)propane,
2,2-bis(3-aminophenyl)-1,1,1,3,3,3-hexafluoropropane,
2,2-bis(3-amino-2-methylphenyl)-1,1,1,3,3,3-hexafluoropropane,
2,2-bis(3-amino-4-methylphenyl)-1,1,1,3,3,3-hexafluoropropane,
2,2-bis(3-amino-2-trifluoromethylphenyl)-1,1,1,3,3,3-hexafluoropropane,
2,2-bis(4-aminophenyl)-1,1,1,3,3,3-hexafluoropropane,
2,2-bis(4-amino-2-methylphenyl)-1,1,1,3,3,3-hexafluoropropane,
2,2-bis(4-amino-3-methylphenyl)-1,1,1,3,3,3-hexafluoropropane,
2,2-bis(4-amino-2-trifluoromethylphenyl)-1,1,1,3,3,3-hexafluoropropane,
2,2-bis(4-amino-3-trifluoromethylphenyl)-1,1,1,3,3,3-hexafluoropropane,
2,2-bis(3-amino-4-trifluoromethylphenyl)-1,1,1,3,3,3-hexafluoropropane,
2,2-bis[(4-aminophenyloxy)methyl]propane,
2,2-bis[(4-amino-2-methylphenyloxy)methyl]propane,
2,2-bis[(4-amino-3-methyphenyloxy)methyl]propane,
2,2-bis[(4-amino-2-trifluoromethylphenyloxy)methyl]propane,
2,2-bis[(4-amino-3-trifluoromethyphenyloxy)methyl]propane,
2,2-bis[4-(3-aminophenyloxy)phenyl]propane,
2,2-bis[4-(3-amino-2-methylphenyloxy)phenyl]propane,
2,2-bis[4-(3-amino-4-methylphenyloxy)phenyl]propane,
2,2-bis[4-(3-amino-2-trifluoromethylphenyloxy)phenyl]propane,
2,2-bis[4-(4-aminophenyloxy)phenyl]propane,
2,2-bis[4-(4-amino-2-methylphenyloxy)phenyl]propane,
2,2-bis[4-(4-amino-3-methylphenyloxy)phenyl]propane, 2,2-bis[4-(4-amino-2-trifluoromethylphenyloxy)phenyl] propane,
2,2-bis[4-(4-amino-3-trifluoromethylphenyloxy)phenyl] propane,
bis[1,2,5,6-tetrafluoro-4-(3-aminophenyloxy)phenyl], bis[1,2,5,6-tetrafluoro-4-(4-aminophenyloxy)phenyl], 2,2-bis(3-aminophenyloxy)phenyl-1,1,1,3,3,3-hexafluoropropane,
2,2-bis(3-amino-2-methylphenyloxy)phenyl-1,1,1,3,3,3-hexafluoropropane,
2,2-bis(3-amino-4-methylphenyloxy)phenyl-1,1,1,3,3,3-hexafluoropropane,
2,2-bis(3-amino-2-trifluoromethylphenyloxy)phenyl-1,1,1,3,3,3-hexafluoropropane,
2,2-bis(3-amino-4-trifluoromethylphenyloxy)phenyl-1,1,1,3,3,3-hexafluoropropane,
2,2-bis(4-aminophenyloxy)phenyl-1,1,1,3,3,3-hexafluoropropane,
2,2-bis(4-amino-2-methylphenyloxy)phenyl-1,1,1,3,3,3-hexafluoropropane,
2,2-bis(4-amino-3-methylphenyloxy)phenyl-1,1,1,3,3,3-hexafluoropropane,
2,2-bis(4-amino-2-trifluoromethylphenyloxy)phenyl-1,1,1,3,3,3-hexafluoropropane,
2,2-bis(4-amino-3-trifluoromethylphenyloxy)phenyl-1,1,1,3,3,3-hexafluoropropane,
alkanediol [bis(3-aminopohenyl) ether],
alkanediol [bis(4-aminopohenyl) ether],
1,4-bis(3-aminophenyloxy)-2,3,5,6-tetrafuruorobenzene, and 1,4-bis(4-aminophenyloxy)-2,4,5,6-tetrafuruorobenzene.

However, the diamines are not limited to those listed above.

These diamines may be used in the form of a mixture of two or more kinds and may have a substituent. The diamines may also be corresponding diisocyanates. In the alkanediols, the alkanes may preferably be those having 2 to 12 carbon atoms.

As a part of diamines, a silicon diamine may also be used. The silicon diamine includes:

1,3-bis(3-aminopropyl)-1,1,1-tetraphenyldisiloxane,
1,3-bis(3-aminopropyl)-1,1,1-tetramethyldisiloxane,
and 1,3-bis(4-aminobutyl)-1,1,1-tetramethyldisiloxane.

(d)Resin Compositions:

As described above, the compounds (1) or (2) can be used as raw materials for resin. Thus, the present invention provides a resin precursor composition containing any of the compounds (1) or (2). The present invention also provides a resin composition (or a resin precursor composition) containing at least one of the polymers (embracing copolymers) described above. The present invention further provides a resin composition containing at least one of the compounds (1) and (2) and the organic polymer. The resin composition (or a resin precursor composition) of the present invention contains from 1 to 90 parts by weight (preferably from 10 to 30 parts by weight) of the organic polymer (or a resin precursor, a raw material) and from 10 to 99 parts by weight (preferably from 70 to 90 parts by weight) of the solvent. Assuming the total weight of the organic polymer and the solvent as 100 parts by weight, other components (e.g., a cross-linking agent, an initiator, a polymerization inhibitor and a plasticizer) may also be optionally contained in an amount of from 0 to 30 parts by weight.

As the organic polymer in the resin composition containing at least one of the compounds (1) and (2) and the organic polymer, various organic polymers may be used. When used in nonlinear optical materials, the organic polymer may include polyacrylates, polymethacrylates, polyacrylamides, polycarbonates, polysiloxanes, polyamides, polyimides, polyesters, polystyrene, polyether ketones, polyether ether ketones, polyphenyl ether ketones, polybenzocyclobutene and polyquinoline.

The resin composition (or a resin precursor composition) containing any of the compounds (1) or (2) includes a product prepared by dissolving or dispersing the compound in a solvent, a dried product thereof, a heat-treated product thereof, a reduced-pressure-treated product thereof, a pressure-treated product thereof, a light-irradiated product thereof, and a cured product thereof. The compounds (1) and (2) may be contained in any form, including all of the forms where the compound is chemically bonded, dissolved and dispersed, or non-dissolved and dispersed.

The form in which the compound (1) or (2) is contained in the resin composition chiefly includes the following three forms:

i. A form in which the compound (1) or (2) reacts with the monomer, polymer or polymer precursor having a reactive functional group to effect covalent bonding, ionic bonding, coordinate bonding or hydrogen bonding to the polymer formed;

ii. A form in which the compound (1) or (2) is dissolved or dispersed in the resin composition containing the polymer; and iii. A form in which the one having the form-i is mixed with an additional polymer.

The resin composition having the above form-i is produced by mixing the compound (1) or (2) with the monomer, polymer or polymer precursor having a reactive functional group, or with a composition containing at least any of these, to allow them to react to effect covalent bonding, ionic bonding, coordinate bonding or hydrogen bonding.

The resin composition having the above form-ii is produced by mixing the compound (1) or (2) with a polymer or polymer composition to dissolve or disperse the former in the latter. Also, a resin precursor composition prepared by mixing the compound (1) or (2) with a monomer capable of forming a polymer, a polymer, a polymer precursor or a composition containing at least any of these to dissolve or disperse the former in the latter may be polymerized to obtain a resin composition having the above form-ii.

(e) Nonlinear optical device:

When the organic polymer of the present invention is put into optical uses, those in which hydrogen atoms (preferably all the hydrogen atoms) of the diamine and acid anhydride have been substituted with fluorine or heavy hydrogen are preferred because of their small light transmission loss. When used for such uses, the light transmission loss commonly increases with an increase in dye concentration. Accordingly, the dye concentration may be adjusted in accordance with service wavelength, structure of optical parts or production processes, whereby a preferable light transmission loss can be selected.

When the organic polymer of the present invention is used for nonlinear optical materials;

(i) it may preferably have a glass transition temperature (Tg) of 200° C. or above in order to prevent characteristics from deteriorating at process temperatures when devices (such as optical switches) and photoelectric mixed circuits are fabricated; and (ii) it may preferably have a light transmission loss of 5 dB/cm or less at wavelengths of from 0.5 to 1.6 $\mu$m used in light transmission.

Accordingly, the above additional polyimide, which is added when the above copolymer is produced, may preferably have;

(i) a glass transition temperature (Tg) of 200° C. or above; and (ii) a light transmission loss of 5 dB/cm or less at wavelengths of from 0.5 to 1.6 µm used; and may more preferably have;

(i) a glass transition temperature (Tg) of 250° C. or above;

(ii) a light transmission loss of 1 dB/cm or less at wavelengths of from 0.7 to 1.6 µm used; and (iii) a refractive-index difference of 0.1 or less between TE mode and TM mode.

When the organic polymer of the present invention is used as a nonlinear optical material, those having an alkylene chain length (i.e., n or m) of from 2 to 12 are chiefly used. Incidentally, if the alkylene chain length is smaller than 3, the material tends to be affected by the motion of the polyimide backbone chain to make it difficult to carry out poling, resulting in a low $r_{33}$ value. Hence, the alkylene chain length may preferably be not smaller than 3. If the alkylene chain length is larger than 4, the motion of the alkylene chain may be so great that it becomes easy to carry out poling. If the alkylene chain length is larger than 9, the relaxation loss at high temperature makes it difficult to maintain the state after poling, resulting in a low $r_{33}$ value. Accordingly, the alkylene chain length of from 4 to 8 is preferred because it is possible to fulfill both the conditions, the readiness of poling and the less relaxation loss, bringing about a high $r_{33}$ value. In particular, it is most preferable that the alkylene chain length is 6.

EXAMPLES

I. Synthesis of Polyimide Precursor or Polyimide (n=6)

Synthesis Example 1: Synthesis of Compound (1c)

(1) Synthesis of N-acetyl-4-bromoaniline:

In an atmosphere of argon, 50 g (290.7 mmols) of 4-bromoaniline was dissolved in 580 ml of methanol, and the solution obtained was cooled to 0° C., and thereafter 32.6g (1.1-fold equivalent weight) of acetic anhydride was dropwise added thereto. Thereafter, the solution obtained was restored to room temperature, followed by stirring for 1 hour, and the crystals deposited were filtered off. To the residue obtained by vacuum concentration of the filtrate, 250 ml of water was added, and the crystals deposited were collected by filtration, which was then washed with water, followed by natural drying to obtain 65.5 g of N-acetyl-4-bromoaniline (yield: 100%; a white solid).

The results of analysis of the compound thus obtained are shown below. Unless particularly noted, the data of 'H-nuclear magnetic resonance (hereinafter "NMR") spectrum in the present specification are data of measurement made using $CDCl_3$ as a solvent and tetramethylsilane as an internal standard.

Melting point: 167.2–168.6° C.; Infrared absorption (hereinafter "IR") spectrum [ν(cm$^{-1}$)]: 3264, 1666, 1600, 1586, 1524, 1482, 1368, 1302, 1252, 1102, 1062, 1040, 1002, 968, 814, 734, 502, 398; $^1$H-NMR Spectrum [δ(ppm)]: 2.17(s, 3H), 7.37(brs, 1H), 7.41(s, 4H)

(2) Synthesis of N-ethyl-4-bromoaniline:

In a stream of argon, 16.3 g (1.4-fold equivalent weight) of lithium aluminum hydride was added to 200 ml of anhydrous tetrahydrofuran (hereinafter "THF"), and the mixture obtained was cooled to 0° C., and thereafter 65.5 g (306.0 mmols) of N-acetyl-4-bromoaniline dissolved in 330 ml of anhydrous THF was slowly dropwise added thereto, followed by heating and reflux for 2 hours. The reaction solution obtained was restored to room temperature, and slowly poured into ice water. Ethyl acetate was added, and the mixture obtained was stirred for a while, followed by suction filtration, and the solid filtered off was washed with ethyl acetate.

The solution used for washing and the filtrate were combined, and then extracted with ethyl acetate. The extract obtained was washed with water, which was thereafter dried with anhydrous magnesium sulfate and then concentrated. The residue thus obtained was distilled (80–85° C./0.3 Torr) to obtain 52.6 g of N-ethtyl-4-bromoaniline (yield: 85.0%; a colorless oily liquid).

The results of analysis of the compound thus obtained are shown below.

Boiling point: 155° C. (0.4 Torr); IR Spectrum [ν(cm$^{-1}$)]:3404, 2968, 2876, 1594, 1492, 1382, 1312, 1280, 1250, 1174, 1144, 1070, 800; $^1$H-NMR Spectrum [δ(ppm)]: 1.22(t, 3H, J=7.1 Hz), 3.08(q, 4H, J=7.1 Hz), 3.57 (brs, 1H), 6.44(d, 2H, J=8.9 Hz), 7.22(d, 2H, J=8.9 Hz)

(3) Synthesis of N-ethyl-N-(6-hydroxyethyl)-4-bromoaniline:

36.8 g (184.1 mmols) of N-ethyl-4-bromoaniline, 48.1 ml (1.5-fold equivalent weight) of N,N-diisopropylethylamine and 28.9 ml (1.2 equivalent) of 6-bromohexanol were mixed, and the mixture obtained was heated at 110° C. for 14 hours in an atmosphere of argon. Water was added to the reaction solution obtained, which was then extracted with ethyl acetate. The organic layer obtained was dried with anhydrous magnesium sulfate and then concentrated. The residue thus obtained was heated under reduced pressure (160° C./0.3 torr), and the components distilled out were removed to obtain 55.6 g of crude N-ethyl-N-(6-hydroxyhexyl)-4-bromoaniline (yield: 100%; a dark-brown oily liquid).

The results of analysis of the compound thus obtained are shown below.

Boiling point: 160° C. (0.3 Torr); IR Spectrum [ν(cm$^{-1}$)]: 3336, 2928, 2864, 1588, 1492, 1362, 1266, 1188, 1046, 798; $^1$H-NMR Spectrum [δ(ppm)]: 1.12(t, 3H, J=7.0 Hz), 1.37(m, 5H), 1.57(m, 4H), 3.21(t, 2H, J=7.6 Hz), 3.33(q, 2H, J=7.0 Hz), 3.64(t, 2H, J=6.4 Hz), 6.50(d, 2H, J=8.9 Hz), 7.23(d, 2H, J=8.9 Hz)

(4) Synthesis of N-ethyl-N-[6-(tetrahydropyran-2-yl)oxyhexyl]-4-bromoaniline:

55.6 g (theoretical molar number: 184.1 mmols) of crude N-ethyl-N-(6-hydroxyhexyl)-4-bromoaniline was dissolved in 247 ml of chloroform. Then 24.6ml (1.5 equivalent) of 3,4-dihydro-2H-pyran and 7.0 g (0.2 equivalent) of pyridinium p-toluenesulfonate monohydrate were added. After displacement with argon, a Dimroth condenser and an argon balloon were attached to carry out reflux with heating for 5 hours. The reaction solution was cooled to room temperature, and a saturated aqueous sodium hydrogencarbonate solution was added thereto to effect neutralization, followed by extracted with chloroform. The organic layer thus formed was dried with anhydrous sodium sulfate and thereafter concentrated under reduced pressure. The residue thus obtained was purified by silica gel column chromatography (developing system: hexane/ethyl acetate=15/1) to obtain 63.3 g of N-ethyl-N-[6-(tetrahydropyran-2-yl)oxyhexyl]-4-bromoaniline (yield: 90%; a colorless oily liquid). IR Spectrum [ν(cm$^{-1}$)]: 2924, 1588, 1492, 1348, 1260, 1174, 1116, 1066, 1022, 906, 864, 800; $^1$H-NMR Spectrum [δ(ppm)]: 1.12(t, 3H, J=7.0 Hz), 1.35–1.95(m, 14H), 3.20(t, 2H, J=7.6 Hz), 3.27–3.51(m, 4H), 3.73(m, 1H), 3.86(m, 1H), 4.57(t, 1H, J=3.6 Hz), 6.50(d, 2H, J=9.1 Hz), 7.24(d, 2H, J=9.1 Hz)

(5) Synthesis of N-ethyl-N-[6-(tetrahydropyran-2-yl) oxyhexyl]3-4-aminocinnamaldehyde:

27.4 g (71.3 mmols) of N-ethyl-N-[6-(tetrahydropyran-2-yl)oxyhexyl]-4-bromoaniline was dissolved in 130 ml of anhydrous THF, and the solution obtained was cooled to −78° C. in an atmosphere of argon, and 100 ml of a 1.57M t-BuLi pentane solution was dropwise added thereto, followed by stirring for 2 hours. To the resulting reaction solution, an anhydrous THF 14.6 ml solution of 11.3 ml (1.5 equivalent) of N,N-dimethylacrlorein was slowly dropwise added, and the mixture obtained was stirred at 78° C. for 2 hours and at room temperature for 2 hours. To the reaction solution, 10 ml of water was added, followed by stirring and thereafter concentration under reduced pressure. Then, 40.7 g of the residue thus obtained was dissolved in 80 ml of chloroform, and then purified by silica gel column chromatography (developing system: chloroform/ethyl acetate=1/0 to 20/1) to obtain 21.4 g of N-ethyl-N-[6-(tetrahydropyran-2-yl)oxyhexyl]-4-aminocinnamaldehyde (yield: 84%; a yellow oily liquid). $^1$H-NMR Spectrum [δ(ppm)]: 1.19(t, 3H, J=7.0 Hz), 1.30–1.95(m, 14H), 3.31(t, 2H, J=7.6 Hz), 3.32–3.54(m, 4H), 3.73(m, 1H), 3.86(m, 1H), 4.57(t, 1H, J=3.4 Hz), 6.52(dd, 1H, J=2.9 Hz, 15.2 Hz), 6.63(dm 2H, J=9.0 Hz), 7.36(d, 1H, J=15.2 Hz), 7.44(d, 2H, J=9.0 Hz), 9.57(d, 1H, J=7.9 Hz).

(6) Synthesis of 2'-hydroxy-2-(methylsulfinyl) acetophenone:

To 28.6 g (60% oily, 3.4 equivalent) of sodium hydride, 447 ml of toluene and 192 ml of N,N-dimethysulfoxide (hereinafter "DMSO") were added in an atmosphere of argon, and the mixture obtained was heated at 80° C. for 1 hour. The reaction solution was cooled to 35° C., and a toluene 220 ml solution of 31.4 g (188.9 mmols) of ethyl salicylate was dropwise added thereto, followed by heating at 80° C. for 2 hours. The resultant reaction solution was cooled to room temperature, and thereafter the toluene was evaporated off. The residue thus obtained was poured into 1,000 ml of ice water, and acetic acid was added to adjust the pH to 4. Crystals thus deposited were collected by filtration, and then washed with water and hexane, followed by natural drying for 1 hour. To 38.5 g of the crude-purified product thus obtained, 350 ml of ethanol was added to effect dissolution with heating using a 90° C. hot water bath, which was then left overnight at room temperature. Crystals thus deposited were collected by filtration, and then washed with ethanol, followed by vacuum drying (60° C./5 torr) for 2 hours to obtain 32.1 g of 2'-hydroxy-2-(methylsulfinyl) acetophenone (yield: 85%). $^1$H-NMR Spectrum [δ(ppm)]: 2.78(s, 3H), 4.36(q, 2H, J=15.3 Hz), 6.97(t, 1H, J=7.8 Hz), 7.00(d, 1H, J=7.8 Hz), 7.55(t, 1H, J=1.5 Hz, 8.0 Hz), 7.76(dd, 1H, J=1.5 Hz, 8.0 Hz), 11.80(s, 1H)

(7) Synthesis of 2-{N-ethyl-N-[6-(tetrahydropyran-2-yl) oxyhexyl]-4-aminostyryl}-4-chromone:

In an atmosphere of argon, 16.6 g (1.1 equivalent) of 2'-hydroxy-2-(methylsulfinyl)acetophenone was dissolved in 100 ml of toluene at 90° C. The mixture obtained was cooled to 55° C., and a toluene 40 ml solution of 0.5 ml (catalytic quantity) of piperidine and 27.3 g (75.9 mmols) of N-ethyl-N-[6-(tetrahydropyran-2-yl)oxyhexyl]-4-aminocinnamaldehyde was added thereto. The resultant mixture was heated at 55° C. for 1 hours, and thereafter refluxed with heating for 2 hours. After cooling to 55° C., 2.3 g (0.15 equivalent) of 2'-hydroxy-2-(methylsulfinyl) acetophenone and 4 drops of piperidine were added to the mixture, which was further refluxed with heating for 2 hours. After cooling to room temperature, a saturated aqueous sodium hydrogencarbonate solution was added thereto to effect neutralization, followed by extraction with ethyl acetate. The organic layer thus formed was washed with saturated aqueous sodium hydrogencarbonate solution, and then dried with anhydrous sodium sulfate, followed by concentration under reduced pressure. Then, 45.1 g of the residue thus obtained was dissolved in 80 ml of chloroform and purified by silica gel column chromatography (developing system: chloroform/ethyl acetate=1/0 to 85/15) to obtain 26.3 g of 2-{N-ethyl-N-[6-(tetrahydropyran-2-yl) oxyhexyl]-4-aminostyryl}-4-chromone (yield: 72%; a brown oily liquid). $^1$H-NMR Spectrum [δ(ppm)]: δ(ppm, CDCl$_3$, Internal Standard: tetramethylsilane) 1.23(t, 3H, J=7.0 Hz), 1.30–1.95(m, 14H), 3.25(t, 2H, J=7.4 Hz), 3.32–3.54(m, 4H), 3.73(m, 1H), 3.86(m, 1H), 4.57(t, 1H, J=3.4 Hz) 6.18(s, 1H), 6.46(d, 2H, J=15.6 Hz), 6.59(d, 2H, J=8.8 Hz), 7.30(dt, 1H, J=0.6 Hz, 7.4 Hz), 7.40(d, 2H, J=8.8 Hz), 7.43(d, 1H, J=1.4 Hz, 8.3 Hz), 7.46(d, 1H, J=15.8 Hz), 7.58(dt, 1H, J=1.6 Hz, 8.4 Hz), 8.13(dd, J=1.4 Hz, 7.8 Hz).

(8) Synthesis of compound (1c)

To 26.3 g (55.2 mmols) of 2-{N-ethyl-N-[6-(tetrahydropyran-2-yl)oxyhexyl]-4-aminostyryl}-4-chromone, 43 ml of acetic anhydride and 4.4 g (1.2-fold equivalent weight) of malononitrile were added, and heated in an atmosphere of argon at 140° C. for 5 hours. Then 1.1 g (0.3 equivalent weight) of malononitrile was added, and the mixture was further heated at 140° C. for 8 hours. After cooling to room temperature and concentration under reduced pressure, a saturated aqueous sodium hydrogencarbonate solution was added to effect neutralization, followed by extraction with ethyl acetate. The organic layer thus formed was washed with saturated aqueous sodium hydrogencarbonate solution, and then dried with anhydrous sodium sulfate, followed by concentration under reduced pressure to obtain 32.7 g of compound (1c) (a red oily liquid). $^1$H-NMR Spectrum [δ(ppm)]: 1.21(t, 3H, J=7.0 Hz), 1.41(m, 4H), 1.66(m, 4H), 2.12(s, 3H), 3.33(t, 2H, J=7.6 Hz), 3.43(q, 2H, J=7.0 Hz), 4.07(t, 2H, J=6.6 Hz), 6.46(d, 2H, J=15.6 Hz), 6.62(d, 2H, J=8.9 Hz), 6.68(s, 1H), 7.38(dt, 1H, J=1.0 Hz, 8.2 Hz), 7.40(d, 2H, J=8.8 Hz), 7.50(dd, 1H, J=1.4 Hz, 8.7 Hz), 7.50(d, 1H, 15.7 Hz), 7.68(dt, 1H J=1.3 Hz, 8.4 Hz), 8.85(dd, J=1.0 Hz, 8.2 Hz).

Synthesis Example 2: Synthesis of compound (1b)

(1) Synthesis of N-ethyl-N-[6-(tetrahydropyran-2-yl) oxyhexyl]-4-formylaniline:

50.0 g (130 mmols) of N-ethyl-N-[6-(tetrahydropyran-2-yl)oxyhexyl]-4-bromoaniline was dissolved in 180 ml of anhydrous tetrahydrofuran in an atmosphere of argon, and the solution obtained was cooled to −78° C. To the reaction solution obtained, 174.4 ml (2.2-fold equivalent weight) of t-butyl lithium (1.64 M, n-pentane solution) was dropwise added, followed by stirring for 1 hour. To the mixture obtained, 12.3 g (1.3-fold equivalent weight) of N,N-dimethylformamide was dropwise added, which was then stirred at room temperature for 2 hours and 30 minutes. The resultant reaction solution was concentrated, and dissolved in 500 ml of ethyl acetate, followed by washing twice with 300 ml of water. The organic layer thus formed was dried with anhydrous sodium sulfate, followed by concentration under reduced pressure. The residue thus obtained was purified by silica gel column chromatography (developing system: hexane/ethyl acetate=4/1) to obtain 34.7 g of N-ethyl-N-[6-(tetrahydropyran-2-yl)oxyhexyl]-4-formylaniline (yield: 80%; a pale-yellow oily liquid). $^1$H-NMR Spectrum [δ(ppm)]: 1.20(t, 3H, J=7.0 Hz), 1.35–1.95(m, 14H), 3.20–3.55(m, 6H), 3.73(m, 1H), 3.86 (m, 1H), 4.57(t, 1H, J=3.6 Hz), 6.65(d, 2H, J=9.7 Hz), 7.71(d, 2H, J=9.7 Hz), 9.69(s, 1H).

(2) Synthesis of 2-methylchromone:

In an atmosphere of argon, 19.5 g (107.0 mmols) of 2'-hydroxy-2-(methylsulfinyl)acetophenone, 5.65 g (3.4 equivalent) of acetaldehyde and 5.0 ml (0.05 equivalent) of piperidine were dissolved in 500 ml of toluene, and the mixture obtained was refluxed with heating for 1 hour and 45 minutes. The reaction solution was cooled to room temperature and concentrated under reduced pressure to remove the toluene. The residue thus obtained was dissolved in 300 ml of ethyl acetate and washed twice with 200 ml of water. The organic layer thus formed was dried with anhydrous sodium sulfate, followed by concentration under reduced pressure. The residue thus obtained was purified by silica gel column chromatography (developing system: hexane/ethyl acetate=4/6) to obtain 14.7 g of 2-methylchromone (yield: 86%; a pale-white pink solid). $^1$H-NMR Spectrum [δ(ppm)]: 2.39(s, 3H), 6.17(s, 1H), 7.37(m, 2H), 7.64(dt, 1H, J=1.7 Hz, 8.1 Hz), 8.18(dd, 1H, J=1.7 Hz, 8.1 Hz)

(3) Synthesis of 2-methyl-α,α-dicyano-4-chromenylidene:

10.0 g (62.4 mmols) of 2-methylchromone and 20.6g (5.0-fold equivalent weight) of malononitrile were added to 250 ml of acetic anhydride, and the mixture obtained was refluxed with heating in an atmosphere of argon for 5 hours and 30 minutes. The reaction solution was cooled to room temperature and concentrated under reduced pressure to remove the acetic anhydride. The residue thus obtained was purified by silica gel column chromatography (developing system: chloroform) to obtain 11.2 g of 2-methyl-α,α-dicyano-4-chromenylidene (yield: 86%; a pale-orange solid). $^1$H-NMR Spectrum [δ(ppm)]: 2.45(s, 3H), 6.72(s, 1H), 7.46(m, 2H), 7.72(dt, 1H, J=1.7 Hz, 8.1 Hz), 8.92(dd, 1H, J=1.7 Hz, 8.1 Hz)

(4) Synthesis of compound (1b):

In an atmosphere of argon, 9.2 g (24.0 mmols) of N-ethyl-N-[6-(tetrahydropyran-2-yl)oxyhexyl]-4-formylaniline, 5.0 g (1.0 equivalent) of 2-methyl-α,α-dicyano-4-chromenylidene and 1.0 ml (0.05 equivalent) of piperidine were dissolved in 200 ml of toluene, and the mixture obtained was refluxed with heating for 5 hour. The reaction solution was cooled to room temperature and concentrated under reduced pressure to remove the toluene. The residue thus obtained was dissolved purified by silica gel column chromatography (developing system: chloroform) to obtain 13.1 g of compound (1b) (yield: 100%; a red solid). $^1$H-NMR Spectrum [δ(ppm)]: 1.20(t, 3H, J=7.0 Hz), 1.25–1.95(m, 14H), 3.20–3.55(m, 6H), 3.73(m, 1H), 3.86 (m, 1H), 4.57(t, 1H, J=3.6 Hz), 6.52(d, 2H, J=15.6 Hz), 6.65(d, 2H, J=8.9 Hz), 6.75(s, 1H), 7.38(dt, 1H, J=1.0 Hz, 8.2 Hz), 7.40(d, 2H, J=8.8 Hz), 7.50(dd, 1H, J=1.4 Hz, 8.7 Hz), 7.50(d, 1H, J=15.7 Hz), 7.68(dt, 1H, J=1.3 Hz, 8.4 Hz), 8.88(dd, 1H, J=1.0 Hz, 8.2 Hz).

Synthesis Example 3: Synthesis of compound (1a)

31.7 g (theoretical molar number: 53.5 mmols) of compound (1c) was dissolved in 190 ml of THF, and 190 ml of a 6N hydrochloric acid solution was added. The mixture obtained was heated in an atmosphere of argon at 65° C. for 2.5 hours. The reaction solution was cooled to room temperature and thereafter concentrated under reduced pressure, followed by extraction with chloroform. The organic layer thus formed was washed with a saturated aqueous sodium hydrogencarbonate solution, and then dried with anhydrous sodium sulfate, followed by concentration under reduced pressure. Then, 35.4 g of the residue thus obtained was dissolved in 80 ml of chloroform and purified by silica gel column chromatography (developing system: chloroform/hexane/diethyl ether=4/3/1 to 4/0/1; light-shielded) to obtain 15.0 g of compound (1a) (yield: 64%; a dark reddish green solid). $^1$H-NMR Spectrum [δ(ppm)]: 1.21(t, 3H, J=7.0 Hz), 1.41(m, 4H), 1.60(m, 5H), 3.33(t, 2H, J=7.6 Hz), 3.43(q, 2H, J=7.0 Hz), 4.07(t, 2H, J=6.6 Hz), 6.50(d, 2H, J=15.6 Hz), 6.64(d, 2H, J=8.9 Hz), 6.70(s, 1H), 7.41(dt, 1H, J=1.0 Hz, 8.2 Hz), 7.43(d, 2H, J=8.8 Hz), 7.52(d, 1H, J=7.5 Hz), 7.55(d, 1H, J=15.7 Hz), 7.69(dt, 1H, J=1.3 Hz, 8.4 Hz), 8.86(dd, J=1.0 Hz, 8.2 Hz).

Synthesis Example 4: Synthesis of compound (1a)

In an atmosphere of argon, 12.6 g (24.0 mmols) of compound (1b) and 0.9 g (0.2 equivalent) of p-toluenesulfonic acid monohydrate were dissolved in 200 ml of ethanol, and the mixture obtained was refluxed with heating for 3 hours. The reaction solution was cooled to room temperature and concentrated under reduced pressure to remove the ethanol. The residue thus obtained was dissolved in 500 ml of chloroform and washed twice with 200 ml of saturated aqueous sodium hydrogencarbonate solution. The organic layer thus formed was dried with anhydrous sodium sulfate, followed by concentration under reduced pressure. The residue thus obtained was purified by silica gel column chromatography (developing system: chloroform/hexane/diethyl ether=4/3/1 to 4/0/1) to obtain 9.3 g of compound (1a) (yield: 88%; a red solid). $^1$H-NMR Spectrum [δ(ppm)]: 1.21(t, 3H, J=7.0 Hz), 1.41(m, 4H), 1.60(m, 5H), 3.33(t, 2H, J=7.6 Hz), 3.43(q, 2H, J=7.0 Hz), 4.07(t, 2H, J=6.6 Hz), 6.50(d, 2H, J=15.6 Hz), 6.64(d, 2H, J=8.9 Hz), 6.70(s, 1H), 7.41(dt, 1H, J=1.0 Hz, 8.2 Hz), 7.43(d, 2H, J=8.8 Hz), 7.52(d, 1H, J=7.5 Hz), 7.55(d, 1H, J=15.7 Hz), 7.69(dt, 1H, J=1.3 Hz, 8.4 Hz), 8.86(dd, 1H, J=1.0 Hz, 8.2 Hz)

Synthesis Example 5: Synthesis of compound (1d)

In an atmosphere of argon, 15.0 g (30.4 mmols) of compound (1a), 6.2 g (1.1-fold equivalent weight) of 2,5-dinitrophenol and 9.6 g (1.2 equivalent) of triphenylphosphine were dissolved in 395 ml of anhydrous THF, and the mixture obtained was stirred at room temperature for 30 minutes, and thereafter 17.2 g (1.3-fold equivalent weight) of a 40% diethylazocarboxylate (hereinafter "DEAD") toluene solution was added, followed by stirring at room temperature for 1 hour. Then, 8.0 g (1.0 equivalent) of triphenylphosphine and 13.2 g (1.0-fold equivalent weight) of 40% DEAD toluene solution were added, and the mixture obtained was stirred at room temperature for 1 hour. Furthermore, 1.7 g (0.3-fold equivalent weight) of 2,5-dinitrophenol, 4.8 g (0.6-fold equivalent weight) of triphenylphosphine and 7.9 g (0.6 equivalent) of 40% DEAD toluene solution were added, and the mixture obtained was stirred at room temperature for 1 hour. The reaction solution was concentrated under reduced pressure, and the residue thus obtained was dissolved in 500 ml of chloroform, followed by addition of 170 g of silica gel, and then concentration under reduced pressure and light shielding. The residue (250g) thus obtained was purified with silica gel column chromatography (developing system: chloroform/ethyl acetate=1/0 to 30/1; light-shielded). Then, 33.2 g of the crude-purified product thus obtained was dissolved in 80 ml of chloroform and was purified by silica gel column chromatography (developing system: chloroform/ethyl acetate=1/0 to 30/1; light-shielded) to obtain 15.7 g of compound (1d) (yield: 85%; a dark reddish green solid). $^1$H-NMR Spectrum [δ(ppm)]: 1.21(t, 3H, J=7.0 Hz), 1.47(m, 2H), 1.55(m, 2H), 1.65(m, 2H), 1.91(quint, 2H, J=7.0 Hz), 3.36(t, 2H, J=7.5 Hz), 3.44(1, 2H, J=7.1 Hz), 4.22(t, 2H, J=6.1 Hz), 6.53(d, 1H, J=15.6 Hz), 6.66(d, 2H, J=8.9 Hz), 6.76(s, 1H), 7.41(dt, 1H, J=1.0 Hz, 8.2 Hz), 7.45(d, 2H, J=8.8 Hz), 7.52(dd, 1H, J=1.2 Hz, 8.3 Hz), 7.55(d, 1H, J=15.7 Hz), 7.70(dt, 1H, J=1.3 Hz, 8.4 Hz), 8.89(dd, J=1.0 Hz, 8.2 Hz).

Synthesis Example 6: Synthesis of compound (2a)

Figure 8:
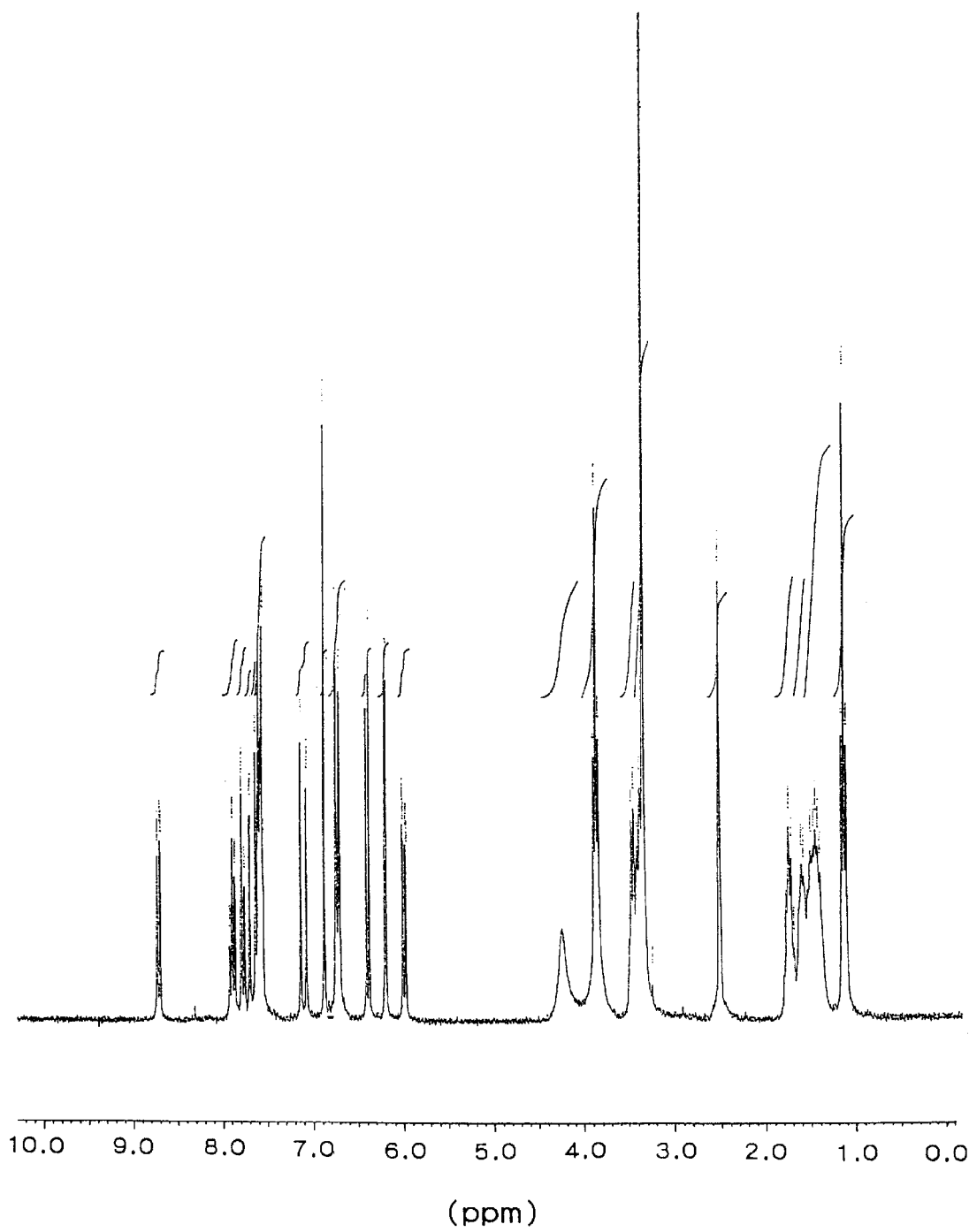
FIG. 8 is a $^1$H-NMR chart of compound 2(a) obtained by Synthesis Example 6.

A mixture of 102.3 g (17.5 equivalent) of tin chloride dihydrate and 380 ml of ethyl acetate were stirred, and an ethyl acetate 380 ml solution of 15.7 g (25.9 mmols) of the compound (1d) was dropwise added thereto at room temperature, followed by stirring at room temperature for 13 hours. The reaction mixture obtained was poured in 1,500 ml of a saturated aqueous sodium hydrogencarbonate solution to effect extraction. The organic layer formed was washed with saturated aqueous sodium hydrogencarbonate solution and brine, and then dried with anhydrous sodium sulfate. To the aqueous layer, 4,000 ml of chloroform and 50 g of Celite were added and stirred, followed by suction filtration using a Buchner funnel laid with Celite. The organic layer obtained by extracting the filtrate was washed with saturated aqueous sodium hydrogencarbonate solution and brine, and then dried with anhydrous sodium sulfate. The residue was washed with 2,000 ml of chloroform. The chloroform solution thus obtained was washed with saturated aqueous sodium hydrogencarbonate solution and brine, and thereafter dried with anhydrous sodium sulfate. All the organic layers were put together and concentrated under reduced pressure, and 15,4 g of the residue thus obtained was dissolved in 60 ml of chloroform, and purified by silica gel column chromatography (developing system: chloroform/ethyl acetate=1/0 to 7/3). The purified product obtained was dissolved in 300 ml of chloroform and was filtered with a filter, followed by concentration under reduced pressure to obtain a residue. This residue was stirred with addition of 500 ml of distilled hexane, followed by filtration and then vacuum drying (0.3 torr) at room temperature to obtain 11.0 g of compound (2a) (yield: 72%; a dark reddish green solid). Thermal stability of this compound was measured with a differential scanning calorimeter to find that it was stable up to 280° C. $^1$H-NMR spectrum of the compound (2a) thus obtained is shown in FIG. 8. $^1$H-NMR Spectrum [δ(ppm)]: 1.20(t, 3H, J=7.0 Hz), 1.45(m, 2H), 1.55(m, 2H), 1.67(m, 2H), 1.83(quint, 2H, J=6.8 Hz), 2.96(brs, 4H), 3.35(t, 2H, J=7.2 Hz), 3.44(q, 2H, J=6.9 Hz), 3.95(t, 2H, J=6.9 Hz), 6.20(dd, 1H, J=2.3 Hz, 8.0 Hz) 6.26(d, 1H, J=2.3 Hz), 6.52(d, 1H, J=15.2 Hz), 6.58(d, 1H, J=8.0 Hz), 6.66(d, 2H, J=8.9 Hz), 6.76(s, 1H), 7.41(dt, 1H, J=1.0 Hz, 8.2 Hz), 7.45(d, 2H, J=8.8 Hz), 7.52(d, 1H, J=7.5 Hz), 7.55(d, 1H, J=15.7 Hz), 7.70(dt, 1H, J=1.3 Hz, 8.4 Hz), 8.89(dd, J=1.0 Hz, 8.2 Hz).

Synthesis Example 7: Synthesis of polyimide precursor (dye density: 15.5 wt.%)

In an atmosphere of nitrogen, 2.0 g (3.665 mmols) of the compound (2a) and 1.7 g (8.495 mols) of bis(4-diaminodiphenyl) ether were dissolved in 28.ml of N,N-dimethylacetamide. To the solution obtained, 5.4mg (12.160 mmols) of 2,2-bis(3,4-dicarboxyphenyl)hexafluoropropane dianhydrate was added at 0° C., followed by stirring at 0° C. for 2 hours and then at room temperature for 4 hours to obtain a polyimide precursor solution.

This solution had a viscosity of about 332 poises. The polyimide precursor thus obtained had an MW of 2.78×105 in terms of polystyrene (elution time: 20.788 minutes). In the present specification, unless particularly noted, the values indicated as molecular weight are those obtained as values in terms of polystyrene, using gel permeation chromatography (hereinafter "GPC") (chromatopack: "Shimadzu C—R$^4$A", available from Shimadzu Corporation; columns: "TOSOH, TSK-GEL, G2000HXL", available from Tosoh Co., Ltd.; developing system: DMF).

To this polyimide precursor solution, 38.0 ml of N,N-dimethylacetamide was added to adjust its viscosity to 15.8 poises. The mixture thus obtained was pressure-filtered using a filter (pore diameter: 0.22 μm) to obtain 64.0 g of a polyimide precursor solution (solid content: 12.8% by weight) having a dye density of 15.5%. In the present specification, the percentage of the weight of atomic groups of the general formula (16) with respect to the total weight of the polymer is regarded as the dye density of the polymer.

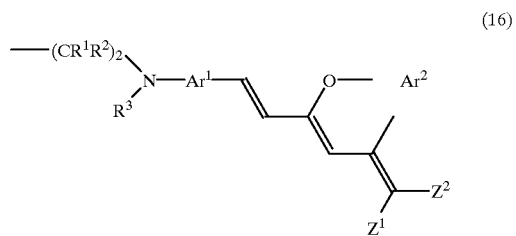

(16)

The polyimide precursor solution thus obtained was spin-coated on a silicon wafer of 5 inches diameter, having a surface formed of a silicon oxide layer, and the coating formed was heated at 100° C. for 2 minutes and thereafter heated to cure in an atmosphere of nitrogen, at 250° C. for 30 hours, subsequently at 280° C. for 15 minutes and further at 290° C. for 10 minutes to form a polyimide film. The polyimide film thus obtained was evaluated using a differential scanning calorimeter to find that it had a glass transition point (Tg) of 245° C. and was stable at 280° C.

It also had a refractive index at 830 nm, of 1.6253 in TM mode and 1.6324 in TE mode, and a Δn of 0.0071. The light transmission loss was 7.99 dB/cm in TM mode and 8.37 dB/cm in TE mode.

Figure 9A:
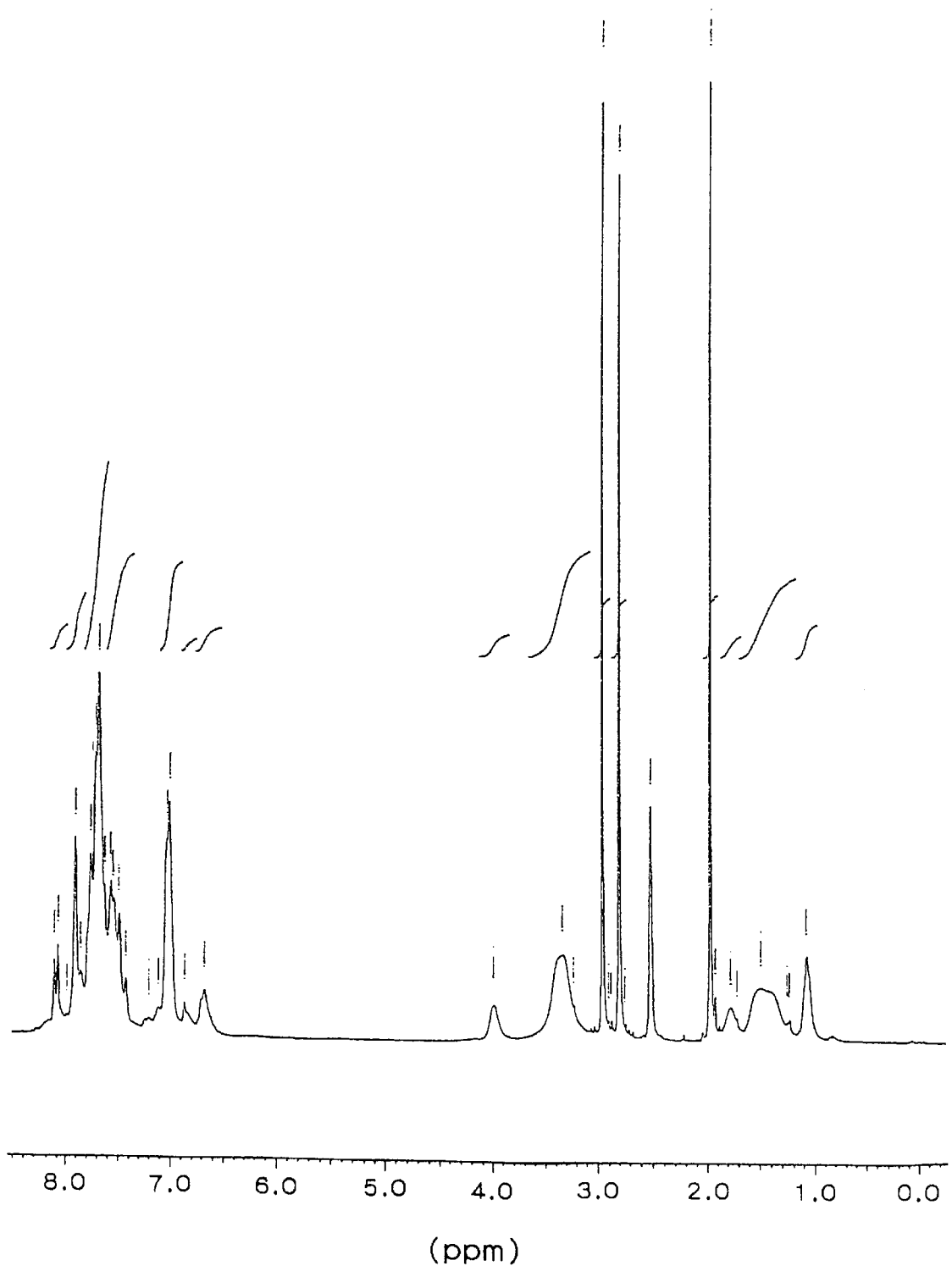
FIGS. 9A and 9B are $^1$H-NMR charts of a polyimide precursor obtained by Synthesis Example 7.
Figure 9B:
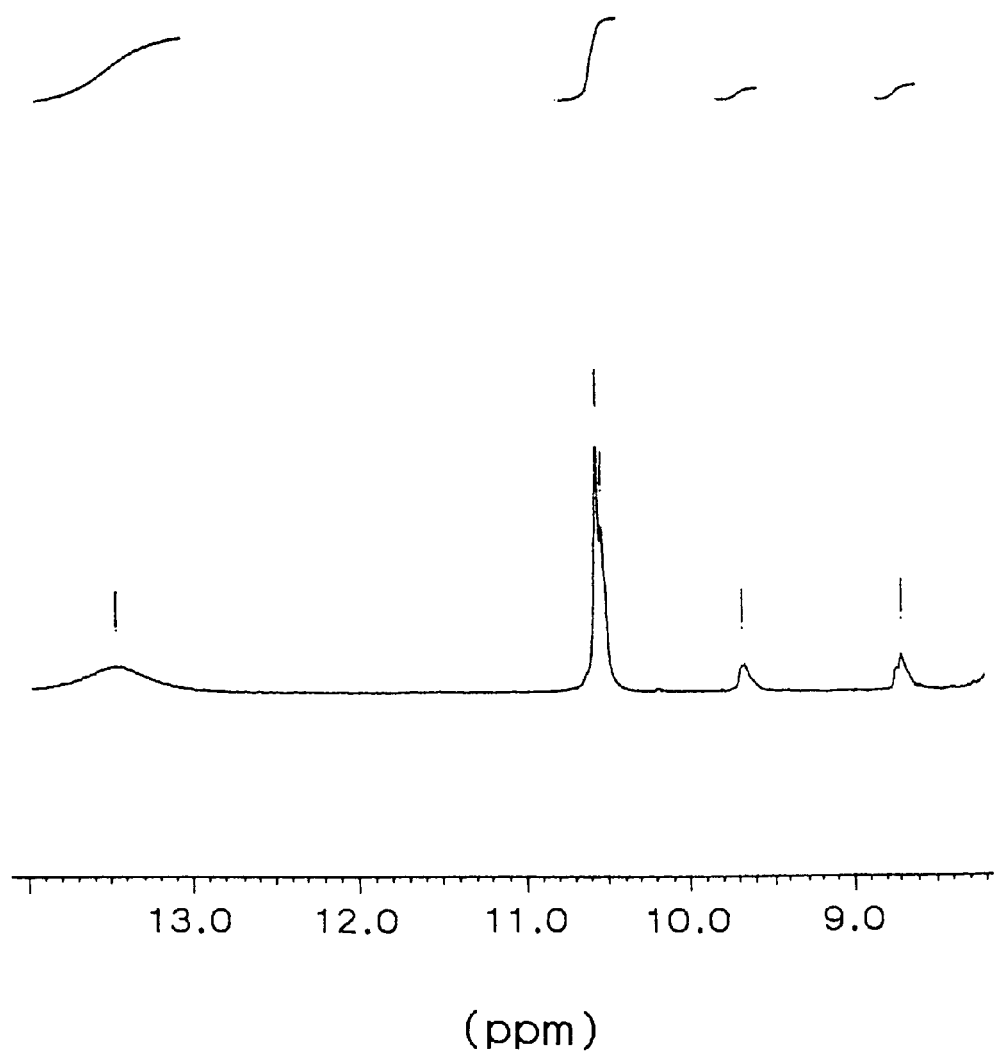

A small amount of this precursor was dropwise added to water, and the solid deposited was collected by filtration, followed by drying under reduced pressure. $^1$H-NMR spectra measured using deuteriodimethyl sulfoxide (DMSO-d6) are shown in FIGS. 9A and 9B.

Synthesis Example 8: Synthesis of polyimide precursor copolymer (dye density: 17.2 wt. %)

(1) Synthesis of polyimide precursor:

In an atmosphere of nitrogen, 103.40 g (0.23 mol) of 2,2-bis(3,4-dicarboxyphenyl) 1,1,1,3,3,3-hexafluoropropane dianhydrate and 46.60 g (0.23 mol) of bis(4-diaminodiphenyl) ether were mixed with 850 g of N,N-dimethylacetamide. The mixture obtained was stirred at room temperature for 6 hours to obtain a polyimide precursor solution (solid content: 15% by weight). This solution had a viscosity of about 80 poises. The molecular weight of the polyimide precursor thus obtained was measured to find that Mn was 1.30×10$^5$, Mw was 4.51×10$^5$, and Mw/Mn was 3.48 in terms of polystyrene (elution time: 21.011 minutes).

The polyimide precursor solution thus obtained was pin-coated on a silicon wafer of 5 inches diameter, having surface formed of a silicon oxide layer, and the coating formed was heated to cure in an atmosphere of nitrogen, at 70° C. for 2 hours, subsequently at 160° C. for 30 minutes and further at 350° C. for 1 hour to form a polyimide film. The polyimide film thus obtained was evaluated using a differential scanning calorimeter to find that it had a glass transition point (Tg) of 298° C. It also had a refractive index at 1,300 nm, of 1.5593 in TM mode and 1.5672 in TE mode, and a Δn of 0.0079. The light transmission loss was 0.52 dB/cm in TM mode and 0.45 dB/cm in TE mode.

(2) Synthesis of copolymer:

The polyimide precursor solution obtained in Synthesis Example 4 and 2.28 g of the polyimide precursor solution obtained in the above (1) were mixed. The mixture obtained was stirred at room temperature for 2 hours, and then stirred at 90° C. for 20 minutes. The mixture thus obtained was pressure-filtered using a filter (pore diameter: 0.22 μm) to obtain 3.0 g of a copolymer polyimide precursor solution (solid content: 16.7% by weight) having a dye density of 17.2%. Here, the proportion (%) of the weight of atomic groups, obtained by excluding oxygen atom content from the atomic groups of the compound of general formula (5) is regarded as the dye density of the polymer.

The molecular weight of the polyimide precursor thus obtained was measured to find that weight-average molecular weight (hereinafter "Mw") was $1.33 \times 10^5$ in terms of polystyrene (elution time: 22.355 minutes).

The polyimide precursor solution thus obtained was spin-coated on a silicon wafer of 5 inches diameter, having a surface formed of a silicon oxide layer, and the coating formed was heated at 100° C. for 2 minutes and thereafter heated to cure in an atmosphere of nitrogen, at 250° C. for 30 hours, subsequently at 280° C. for 15 minutes and further at 290° C. for 10 minutes to form a polyimide film. The polyimide film thus obtained was evaluated using a differential scanning calorimeter to find that it had a glass transition point (Tg) of 237° C. and was stable at 280° C.

It also had a refractive index at 830 nm, of 1.6296 in TM mode and 1.6366 in TE mode, and a Δn of 0.0070. The light transmission loss was 11.42 dB/cm in TM mode and 12.19 dB/cm in TE mode.

Example 1

Formation of Polyimide Copolymer Film

The polyimide precursor solution obtained in Synthesis Example 8 was spin-coated on a silicon wafer of 5 inches diameter, having a surface formed of a silicon oxide layer, and the coating formed was heated to cure in an atmosphere of nitrogen, at 85° C. for 2 minutes, at 250° C. for 30 minutes, at 280° C. for 15 minutes and further at 290° C. for 10 minutes to form a film having a layer thickness of 5 μm, consisting of the polyimide copolymer, and whose dye density is 17.2%. The glass transition point, refractive index at 830 nm and light transmission loss of the polyimide film thus obtained were measured.

The polyimide precursor solution obtained was also spin-coated on a glass substrate on the surface of which an ITO (Indium Tin Oxide) film was formed by vacuum deposition, and the coating formed was heated to cure in an atmosphere of nitrogen, at 85° C. for 2 minutes, at 250° C. for 30 minutes, at 280° C. for 15 minutes, and further at 290° C. for 10 minutes to obtain a polyimide film having a layer thickness of 5 μm. On the polyimide film thus obtained, an aluminum electrode (diameter: 3 mm) was formed by vacuum deposition, and was subjected to poling at 250° C. while applying 100 V/μm voltage, then, electro-optic constant $r_{33}$ at 830 nm was measured. The results of measurement are shown in Table 1.

A preferable light transmission loss can be selected by controlling the dye density. For example, in the case of a polyimide copolymer shown in Table 1, the dye density can be made large by 17% by weight when it is intended to make the propagation loss not greater than 5 dB at 830 nm.

TABLE 1

| Dye Density (%) | $r_{33}$ (pm/V) | Refractive Index | | Propagation loss(dB) | |
| --- | --- | --- | --- | --- | --- |
| | | TE | TM | TE | TM |
| 9.9 | 4.75 | 1.6100 | 1.6038 | 1.9 | 1.9 |
| 14.0 | 6.70 | 1.6235 | 1.6163 | 3.9 | 4.9 |
| 15.5 | 8.80 | 1.6317 | 1.6239 | 3.8 | 4.2 |
| 17.2 | 9.10 | 1.6366 | 1.6297 | 4.4 | 4.9 |
| 20.0 | 10.86 | 1.6466 | 1.6389 | 7.1 | 9.6 |
| 30.0 | 13.90 | 1.6784 | 1.6703 | 14.5 | 12.8 |

Example 2

Fabrication of Optical Device (1) Formation of a lower electrode

First, on a surface of a 6 inch silicon wafer 101 (FIG. 7(a)), an aluminum type metal film 102a (thickness: 0.1 μm) was formed (FIG. 7(b)), and a resist 103 was coated on its surface, followed by exposure and development to form the resist into a pattern (FIG. 7(c)). Thereafter, the metal layer 102a was etched and the resist was stripped off to form a lower electrode 102 (FIG. 7(d)).

(2) Formation of a lower clad layer

Figure 7:
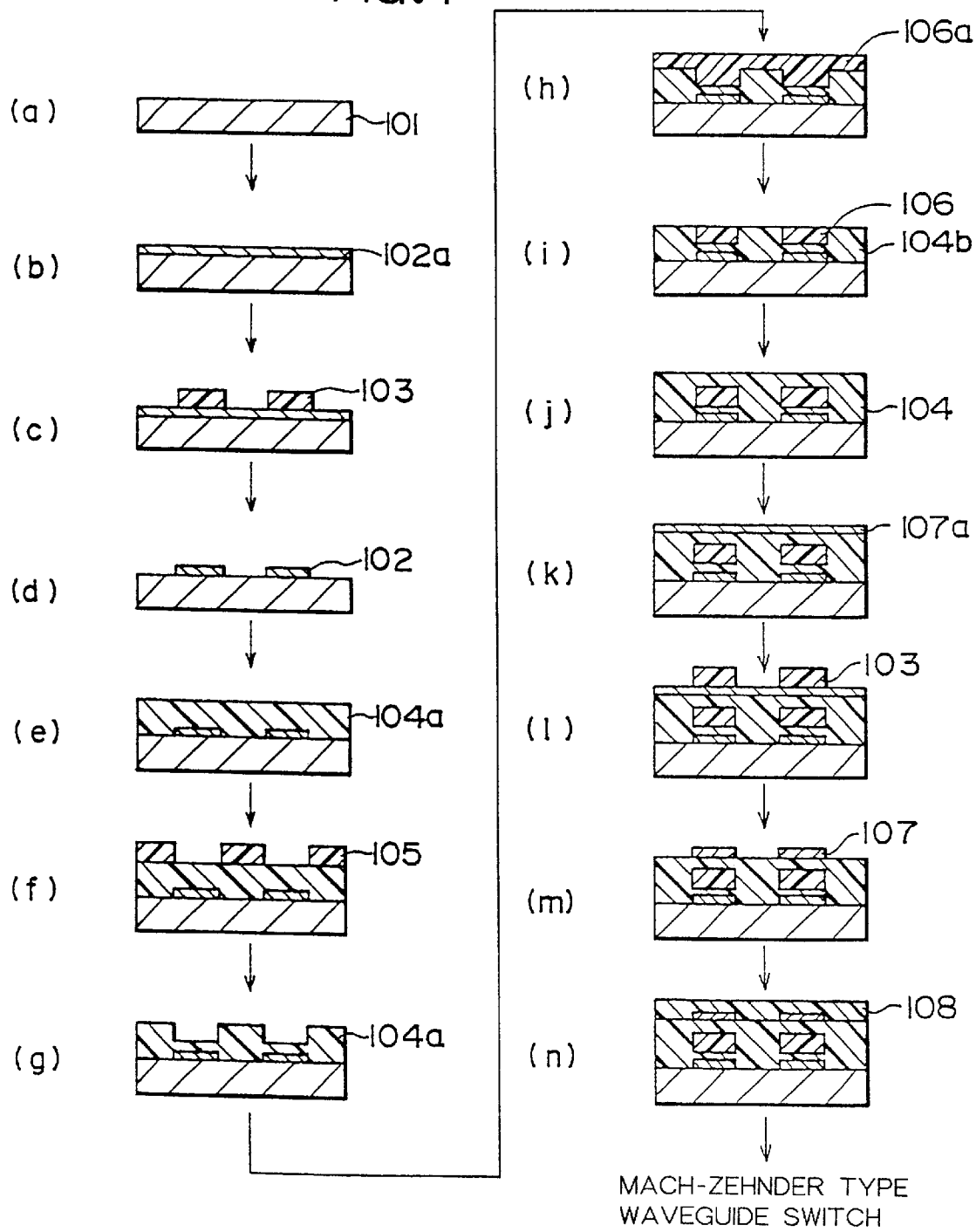
FIG. 7, (a) to (n), illustrates a process for fabricating an optical component part in Example 2.

Next, a polyimide precursor solution (having a TM refractive index of 1.625 after heat curing) was spin-coated on a surface of the wafer 101 so as to cover the lower electrode 102, followed by heat curing to form a polyimide layer 104a (FIG. 7 (e)). A resist was coated on a surface of this polyimide layer 104a, and the resist coated was exposed in a stated pattern, followed by development (FIG. 7(f)). Thereafter, the polyimide layer 104a was etched and the resist was stripped off to form a lower clad layer 104b having concave portions corresponding to the core pattern of a Mach-Zehnder type waveguide switch (FIG. 7(g)).

(3) Formation of a core

The polyimide precursor copolymer solution obtained in Synthesis Example 8 was spin-coated on a surface of the lower clad layer 104b so as to cover the concaves, followed by heating at 85° C. for 2 minutes, 250° C. for 30 minutes, 280° C. for 15 minutes and at 290° C. for 10 minutes to cure to form a polyimide layer 106a (FIG. 7(h)). Thereafter, the surface of the polyimide layer 106a was abraded until the lower clad layer 104b was laid bare. Thus, a core 106 of the core pattern of a Mach-Zehnder type waveguide was formed (FIG. 7(i)).

(4) Formation of an upper clad layer In order to cover the core 106, the same polyimide precursor solution as used in the step (2) was spin-coated, followed by heat curing to form an upper clad layer to make it integral with the lower clad layer 104b already formed (FIG. 7(j)). Thus, the surface of the core 106 was covered with the clad layer 104.

(5) Formation of an upper electrode

Next, on a surface of the clad layer 104, an aluminum type metal film 107a (1.0 μm) was formed (FIG. 7 (k)), and a resist 103 was coated on its surface, followed by exposure and development to form the resist into a pattern (FIG. 7(l)). Thereafter, the metal layer 107 a was etched and the resist was stripped off to form an upper electrode 107 (FIG. 7(m)). Finally, the clad layer surface was coated with resin so as to cover the upper electrode 107, to provide a cover coat layer 108 (FIG. 7(n)).

(6) Stripping of a protective film

The resulting wafer was subjected to poling, and thereafter a protective layer was spin-coated, followed by heat curing and then dicing, and the protective film was stripped off to obtain a Mach-Zehnder type waveguide switch.

What is claimed is:

1. A heteroaromatic compound represented by the following general formula (1):

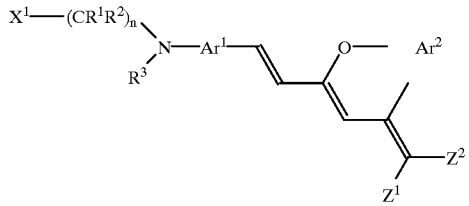

(1)

wherein $Ar^1$ and $Ar^2$ each represents a divalent aromatic group; $R^1$, $R^2$ and $R^3$ each represents a group independently selected from a hydrogen atom, an alkyl group and an aromatic group; $X^1$ represents a monovalent organic group; n represents an integer of 3 to 12; and $Z^1$ and $Z^2$ each represents a group independently selected from electron attractive functional groups, and are each a monovalent functional group, or are each a divalent or greater-valent functional group and combine with each other.

2. The heteroaromatic compound according to claim 1, which is represented by the following general formula (7):

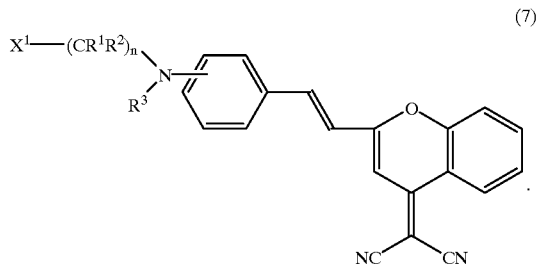

(7)

3. A heteroaromatic compound represented by the following general formula (2):

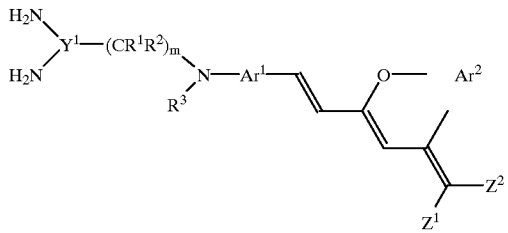

(2)

wherein $Ar^1$ and $Ar^2$ each represents a divalent aromatic group; $R^1$, $R^2$ and $R^3$ each represents an atom or a group independently selected from a hydrogen atom, an alkyl group and an aromatic group; $Y^1$ represents a trivalent organic group; m represents an integer of 2 to 12; and $Z^1$ and $Z^2$ each represents a group independently selected from electron attractive functional groups, and are each a monovalent functional group, or are each a divalent or greater-valent functional group and combine with each other.

4. The heteroaromatic compound according to claim 3, wherein said $Y^1$ is represented by the following structural formula (8):

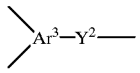

(8)

wherein $Ar^3$ represents a trivalent aromatic group, and $Y^2$ represents a divalent functional group.

5. The heteroaromatic compound according to claim 3, which is represented by the following general formula (9):

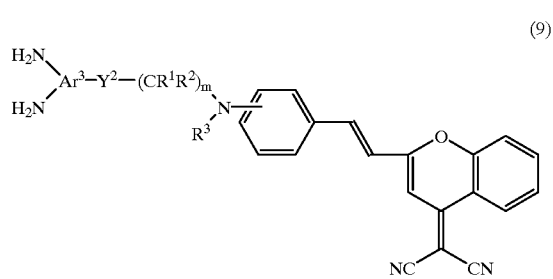

(9)

wherein $R^1$, $R^2$ and $R^3$ each represents an atom or a group independently selected from a hydrogen atom, an alkyl group and an aromatic group; m represents an integer of 2 to 12; $Ar^3$ represents a trivalent aromatic group; and $Y^2$ represents a divalent functional group.

6. A heteroaromatic compound represented by the following general formula (10):

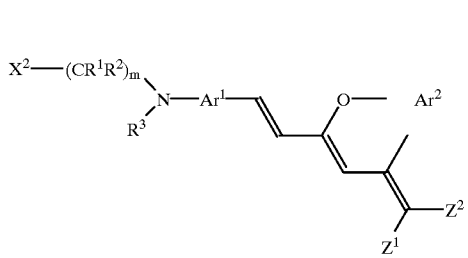

(10)

wherein $Ar^1$ and $Ar^2$ each represents a divalent aromatic group; $R^1$, $R^2$ and $R^3$ each represents an atom or a group independently selected from a hydrogen atom, an alkyl group and an aromatic group; $X^2$ represents a monovalent organic group having at least one of an aliphatic ring and an aromatic ring; m represents an integer of 2 to 12; and $Z^1$ and $Z^2$ each represents a group independently selected from electron attractive functional groups, and are each a monovalent functional group, or are each a divalent or greater-valent functional group and combine with each other.

7. The heteroaromatic compound according to claim 6, which is represented by the following general formula (11):

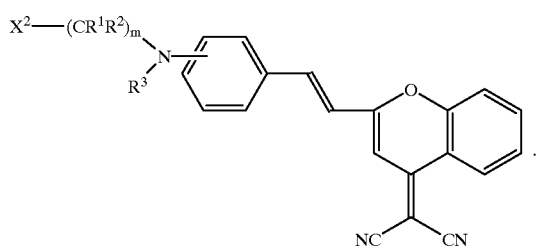

(11)

8. An organic polymer having an atomic group represented by the following general formula (3):

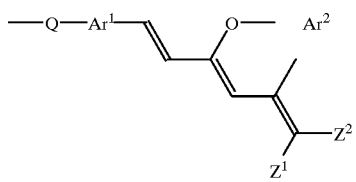

(3)

wherein $Ar^1$ and $Ar^2$ each represents an aromatic group independently selected; Q represents an electron donative functional group; and $Z^1$ and $Z^2$ each represents a group independently selected from electron attractive functional groups, and are each a monovalent functional group, or are each a divalent or greater-valent functional group and combine with each other.

9. The organic polymer according to claim 8, wherein said atomic group is represented by the following general formula (12):

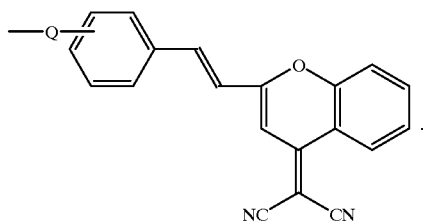

(12)

10. The organic polymer according to claim 8, wherein said Q comprises an atomic group represented by the following general formula (4):

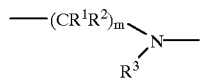

(4)

wherein $R^1$, $R^2$ and $R^3$ each represents a hydrogen atom or a monovalent organic group; and m represents an integer of 2 to 12.

11. The organic polymer according to claim 8, which is a polyimide or a polyimide precursor.

12. The organic polymer according to claim 8, which is obtained by reacting a heteroaromatic compound represented by the following general formula (2):

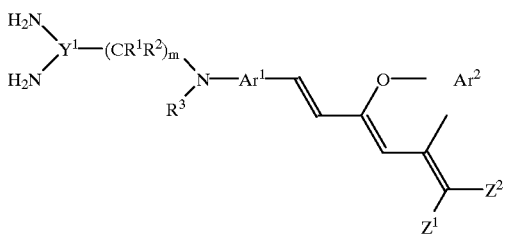

(2)

wherein $Ar^1$ and $Ar^2$ each represents a divalent aromatic group; $R^1$, $R^2$ and $R^3$ each represents an atom or a group independently selected from a hydrogen atom, an alkyl group and an aromatic group; $Y^1$ represents a trivalent organic group; m represents an integer of 2 to 12; and $Z^1$ and $Z^2$ each represents a group independently selected from electron attractive functional groups, and are each a monovalent functional group, or are each a divalent or greater-valent functional group and combine with each other.

13. The organic polymer according to claim 12, which is obtained by allowing the heteroaromatic compound represented by the above general formula (2) to react with a carboxylic anhydride.

14. A copolymeric polyimide precursor produced by mixing and heating at least two antecedent polyimide precursors, wherein at least one of said antecedent polyimide precursors is the organic polymer according to claim 13.

15. A copolymer obtained by heat-curing a composition containing the copolymeric polyimide precursor according to claim 14.

16. A resin composition comprising the heteroaromatic compound according to claim 1.

17. An organic polymer obtained by curing the resin composition according to claim 16.

18. A resin composition comprising the heteroaromatic compound according to claim 3.

19. An organic polymer obtained by curing the resin composition according to claim 18.

20. A resin composition comprising the heteroaromatic compound according to claim 6.

21. An organic polymer obtained by curing the resin composition according to claim 20.

22. An optical device at least a part of which comprises the organic polymer according to claim 8.

* * * * *